US009259464B2

(12) United States Patent
Webster et al.

(10) Patent No.: US 9,259,464 B2
(45) Date of Patent: **\*Feb. 16, 2016**

(54) PHARMACEUTICAL PRODUCT COMPRISING MITE ALLERGEN EXTRACT(S) AND A METHOD FOR THE MANUFACTURE THEREOF

(75) Inventors: Heather M. Webster, Spokane, WA (US); Jason Daniel Frey, Seattle, WA (US); Trena L. Repp, Spokane, WA (US); Craig T. Grass, Spokane, WA (US); David Rowles, Spokane, WA (US); Gary Smith, Hayden Lake, ID (US); Domingo Barber Hernandez, Madrid (ES); Fernando Juan Vidales, Madrid (ES); Carmen Arteaga Vazquez, Madrid (ES); Juan Carlos Moreno Segura, Madrid (ES); Maria Jose Chamorro Salillas, Madrid (ES)

(73) Assignee: ALK-Abelló A/S, Horsholm (DK)

( * ) Notice: Subject to any disclaimer, the term of this patent is extended or adjusted under 35 U.S.C. 154(b) by 35 days.

This patent is subject to a terminal disclaimer.

(21) Appl. No.: 13/314,024

(22) Filed: Dec. 7, 2011

(65) Prior Publication Data

US 2012/0076825 A1  Mar. 29, 2012

Related U.S. Application Data

(63) Continuation-in-part of application No. PCT/EP2011/059210, filed on Jun. 3, 2011.

(60) Provisional application No. 61/351,164, filed on Jun. 3, 2010.

(30) Foreign Application Priority Data

Jun. 3, 2010   (EP) .................................... 10164879

(51) Int. Cl.
```
A23J 1/00      (2006.01)
A61K 35/12     (2015.01)
A61K 35/64     (2015.01)
A61K 39/35     (2006.01)
A61K 39/36     (2006.01)
C07K 1/00      (2006.01)
C07K 14/00     (2006.01)
C07K 16/00     (2006.01)
C07K 17/00     (2006.01)
A61K 9/00      (2006.01)
A61K 9/20      (2006.01)
A61K 35/646    (2015.01)
```
(52) U.S. Cl.
CPC .............. *A61K 39/35* (2013.01); *A61K 9/0056* (2013.01); *A61K 9/2063* (2013.01); *A61K 9/2095* (2013.01); *A61K 35/646* (2013.01)

(58) Field of Classification Search
None
See application file for complete search history.

(56) References Cited

U.S. PATENT DOCUMENTS

| 5,773,010 | A | 6/1998 | Oka et al. | |
|---|---|---|---|---|
| 7,704,532 | B1 | 4/2010 | Smith | |
| 8,312,841 | B2 | 11/2012 | Vazquez et al. | |
| 2003/0059445 | A1 | 3/2003 | Andre et al. | |
| 2003/0118670 | A1 | 6/2003 | Smith | |
| 2004/0166123 | A1* | 8/2004 | Jacobi et al. | 424/275.1 |
| 2006/0210590 | A1* | 9/2006 | Hernandez et al. | 424/275.1 |
| 2010/0024048 | A1 | 1/2010 | Vazquez et al. | |

FOREIGN PATENT DOCUMENTS

| CA | 2010177 | 3/2000 |
|---|---|---|
| CN | 100536918 C | 9/2009 |

OTHER PUBLICATIONS

PCT/EP2011/059210 International Search Report and Written Opinion dated Jul. 27, 2011.
Heymann et al., "Antigenic and Structural Analysis of Group II Allergens (Der f II and Der p II) from House Dust Mites (*Demartophagoides* spp)," Journal of Allergy and Clinical Immunology, vol. 83, No. 6, pp. 1055-1067 (1989).
Yasueda et al., "Estimation of Der p and Der fl quantities in the reference preparations of *Dermatophagoides* mite extracts," Clinical and Experimental Allergy, vol. 24, No. 11, pp. 1030-1035 (1994).
Wahn et al., "Prospective Study on Immunologic Changes induced by Two Different *Dermatophagoides pteronyssinus* extracts prepared from whole culture and mite bodies" Journal Allergy Clin. Immunology, vol. 82, No. 3 Part 1, (1988).
Arlian et al., "Investigations of Culture Medium-free House Dust Mites: III. Antigens and Allergens of Body and Fecal Extract *Dermatophagoides farinae*," Journal Allergy Clinical Immunology, vol. 79, No. 3, pp. 457-466 (1987).
Batard et al, "Production and Proteomic Characterization of Pharmaceutical-Grade *Dermatophagoides pteroynyssinus* and *Dermatophagoides farinae* Extracts for Allergy Vaccines," International Archives of Allergy and Immunology, vol. 140, pp. 295-305 (2006).
Meyer et al., "Comparison of the Levels of the Major Allergens Der p I and Der p II in Standardized Extracts of the House Dust Mite, *Dermatophagoides pteronyssinus*," Clinical and Experimental Allergy, vol. 24, No. 11 (1994).

(Continued)

*Primary Examiner* — Nora Rooney
(74) *Attorney, Agent, or Firm* — Womble Carlyle Sandridge & Rice, LLP

(57) ABSTRACT

The invention relates to a pharmaceutical product comprising an allergen extract or an allergoid thereof for the treatment and/or prevention of allergy and allergic asthma caused by house dust mites, which extract comprises at least one extract of mite bodies selected from the following groups a)-b): a) An extract of Der p mite bodies, and b) An extract of Der f mite bodies, and at least one extract of mite cultures selected from the following groups c)-g): c) An extract of Der p faecal particles, d) An extract of Der f faecal particles, e) An extract of Der f whole mite culture, f) An extract of an Der p whole mite culture, and g) a combination of extracts c) to f).

43 Claims, 1 Drawing Sheet

(56) References Cited

OTHER PUBLICATIONS

Plunkett et al., "Standardization and Characterization of US House Dust Mite Extracts" (Poster).

Pastorello et al., "Clinical Efficacy of the ALK House Dust Mite Allergy Immunotherapy Tablet Correlates with Immunological Endpoints" (Abstract).

Lockey and Lenford, "Mite Allergens," Allergens and Allergen Immunotherapy, Clinical Allergy and Immunology Series 21, $4^{th}$ Edition, p. 161-164 (2008).

Lockey and Lenford, Allergens and Allergy Immunotherapy, Clinical Allergy and Immunology Series 21, $4^{th}$ Edition, p. 286 (2008).

* cited by examiner

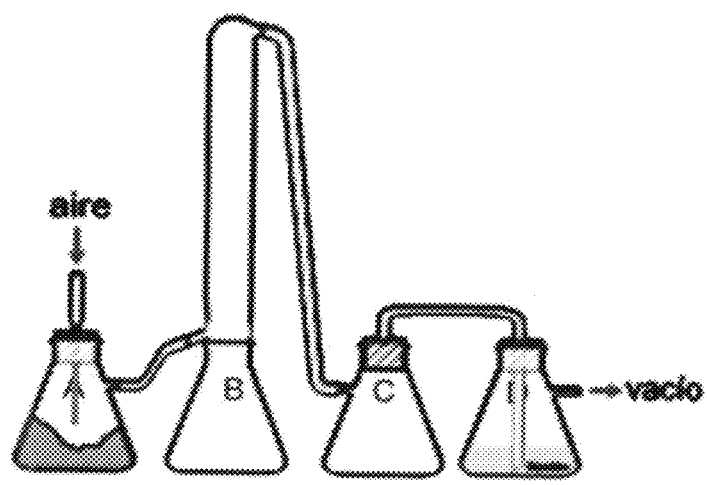

```
                        SEQUENCE LISTING

<160> NUMBER OF SEQ ID NOS: 5

<210> SEQ ID NO 1
<211> LENGTH: 17
<212> TYPE: PRT
<213> ORGANISM: Dermatophagoides pteronyssinus

<400> SEQUENCE: 1

Thr Asn Ala Cys Ser Ile Asn Gly Asn Ala Pro Ala Glu Ile Asp Leu
1               5                   10                  15

Arg

<210> SEQ ID NO 2
<211> LENGTH: 33
<212> TYPE: PRT
<213> ORGANISM: Dermatophagoides farinae

<400> SEQUENCE: 2

Asn Ser Trp Asp Thr Thr Trp Gly Asp Ser Gly Tyr Gly Tyr Phe Gln
1               5                   10                  15

Ala Gly Asn Asn Leu Met Met Ile Glu Gln Tyr Pro Tyr Val Val Ile
            20                  25                  30

Met
```

```
<210> SEQ ID NO 3
<211> LENGTH: 16
<212> TYPE: PRT
<213> ORGANISM: Dermatophagoides pteronyssinus

<400> SEQUENCE: 3

Val Leu Val Pro Gly Cys His Gly Ser Glu Pro Cys Ile Ile His Arg
1               5                   10                  15

<210> SEQ ID NO 4
<211> LENGTH: 17
<212> TYPE: PRT
<213> ORGANISM: Dermatophagoides farinae

<400> SEQUENCE: 4

Gly Lys Pro Phe Thr Leu Glu Ala Leu Phe Asp Ala Asn Gln Asn Thr
1               5                   10                  15

Lys

<210> SEQ ID NO 5
<211> LENGTH: 14
<212> TYPE: PRT
<213> ORGANISM: Dermatophagoides farinae

<400> SEQUENCE: 5

Gly Ile Glu Tyr Ile Gln Gln Asn Gly Val Val Glu Glu Arg
1               5                   10
```

PHARMACEUTICAL PRODUCT COMPRISING MITE ALLERGEN EXTRACT(S) AND A METHOD FOR THE MANUFACTURE THEREOF

CROSS REFERENCE RELATED APPLICATIONS

This application is a continuation in part of PCT/EP2011/059210, filed Jun. 3, 2011, which claims priority to EP10164879.8 filed Jun. 3, 2010 and U.S. provisional application No. 61/351,164 filed Jun. 3, 2010, all of which are hereby incorporated by reference in their entirety.

FIELD OF THE INVENTION

The invention relates to a pharmaceutical product suitable for the treatment and/or prevention of house dust mite allergy and allergic asthma caused by house dust mites comprising mite allergen and a method for the manufacture thereof.

BACKGROUND OF THE INVENTION

Allergy is a major health problem in countries with a Western lifestyle. Furthermore, the prevalence of allergic disease is increasing in these countries. Although allergy in general may not be considered a life-threatening disease, asthma annually causes a significant number of deaths. An exceptional prevalence in about 30% of teenagers conveys a substantial loss in quality of life, working days and money, and warrants a classification among major health problems in the Western world.

Clinical allergy manifestation and symptoms manifest themselves in several ways and may vary depending on the sensitized individual and the allergy inflicted. Common symptoms are edema, itching, redness and running of the eyes and nose (rhinitis and conjunctivitis) and symptoms of the upper and lower airway such as wheezing, coughing, shortness of breath, skin conditions like eczema, urticaria and itching. Other symptoms like fatigue or insomnia are also experienced. Symptomatic treatment aims at reducing or affecting severity of the symptoms or reducing the need for other drugs given in parallel. Symptomatic drugs include antihistamines like $H_1$ and $H_2$ receptor antagonists, intranasal and systemic corticosteroids, non-steroid anti-inflammatory drugs, nasal decongestants like adrenoceptor agonists. Treatment and relief of one or more allergic symptoms and/or the reduction in the need for other medication is a further object of this invention.

Allergen specific immunotherapy (also referred to as allergen immunotherapy, allergy immunotherapy, specific allergy vaccination (SAV), hyposensitization or desensitization) is a causal treatment of allergic disease. It interferes with basic immunological mechanisms resulting in persistent or long term improvement of the patients' immune status. Thus, the protective effect of specific allergy vaccination extends beyond the treatment period in contrast to symptomatic drug treatment. Some patients receiving the treatment are cured, and in addition, most patients experience a relief in disease severity and symptoms experienced, or at least an arrest in disease aggravation. Allergen immunotherapy also has preventive effects reducing the risk of hay fever developing into asthma, and reducing the risk of developing new sensitivities.

Conventional allergen immunotherapy is carried out using multiple administration of allergen applied over an extended time period.

A long standing use of allergen immunotherapy is via the injection route (also called SCIT, SIT or subcutaneous immunotherapy). Commonly, allergen is administered via the subcutaneous route in incremental doses until a maintenance dose is reached, but also treatment regimens with cluster administration or without up-dosing are used. Allergen may be administered for a period up till 3 years or more before treatment is completed or ceased depending on the treatment schedule applied.

An alternative administration route is sublingual (SLIT) administration which is more convenient for the patients as administration may be carried out at home.

The immunotherapy products for use in immunotherapy typically comprise the allergen that causes the allergy in the patient or derivatives thereof as the active ingredient, which may be formulated in various ways according to the administration route of choice such as aqueous formulations, aluminum hydroxide suspensions or allergoids. The active ingredient may for example be an aqueous extract of pollen containing pollen allergens and/or aqueous extract of mites containing mite allergens.

The most important house dust mites belonging to the family of Pyroglyphidae include *Euroglyphus maynei, Dermatophagoides pteronyssinus* and *Dermatophagoides farinae*. These are found in most of the world including Europe, USA, China and many other counties and allergy and allergic asthma caused by house dust mites is a common disease afflicting 25% of the population.

Some patients are sensitized to *Euroglyphus maynei, Dermatophagoides pteronyssinus*, some others to *Dermatophagoides farinae* and others to both species.

Patients are normally sensitized (although to a variable degree) to the two major allergens in house dust mites, namely group 1 allergen and/or group 2 allergen.

House dust mites contain more than 20 different allergens. However, the two major allergens group 1 and group 2 are the most important allergens because of the frequency of patients sensitized to these two allergens, the amount of IgE produced in response to these allergens and the content thereof in natural extracts.

In allergen immunotherapy patients are treated with allergens that they are sensitized to. The ability of allergens to elicit IgE mediated immunologically responses makes it important to control the allergen content especially group 1 and group 2 allergens in the allergen extracts administered to allergic patients to avoid side effects.

The group 1 and 2 allergens from Der f and Der p are closely related but not identical, see Allergens and Allergen Immunotherapy, Clinical Allergy and Immunology Series 21, Lockey and Ledfors, $4^{th}$ ed., page 162-164).

All the products on the market today for immunotherapy of patients with house dust mite allergy comprises aqueous allergen extracts containing group 1 and group 2 mite allergen. Many products contain extracts of both *Dermatophagoides pteronyssinus* and *Dermatophagoides farinae*.

Mite allergen extracts are usually prepared by cultivation of mites in a suitable mite medium followed by extraction of the whole mite culture or extraction of a mite body fraction thereof, Allergens and Allergy Immunotherapy, Fourth Edition, Clinical Allergy and Immunotherapy, series 21, Ed: R. F. Lockey and D. K. Ledfors, page 286.

In the manufacture of allergen extract it is important to control the variability and to achieve consistency and reproducibility for optimal safety and efficacy in a subsequent clinical setting. Standardization of allergen extract are is a complex matter and in principle involves the entire production chain of processes including establishment of robust and reproducible manufacturing procedures, see Allergy Methods and Protocols, Jones and Lympany (2008), chapter 12 and 13. Because of the IgE binding capacity of an allergen extract is related to the content of one or a few major allergens the general standardization strategy normally involves standardizing the extract in respect to content of a selection of these major allergens further to overall IgE binding potency and composition. Relevant method for assays to access allergen extracts are well known in the art and include immunoelectrophoresis assay such as CIE, CRIE, FRIE, CLIE, quantification methods using mono- or polyspecific antibodies such as SRID, RIS, QIE as well as methods of making standardization references. International standards exist to a limited extent, one example being the FDA; CBER reference provided for extract manufactures to standardize against and label their product with resulting in a biopotency label of AI or BAU (Allergy Units or Bioequivalent Allergy Units, see FDA DOCKET NO. 94N-00121 (1993) "Methods of the allergenics products testing Laboratory).

There is considerable batch to batch variation in the amount by weight of group 1 and group 2 allergens in allergen extracts and the amount by weight of group 1 allergen in these allergen extracts is typically higher than the amount of group 2 allergen by weight.

It is well known that the house dust mite group 1 and group 2 allergens are found in both the bodies of the mite and in the faecal particles produced by the mites during cultivation. It is also known that group 1 allergen is associated with the faecal particles and the group 2 allergen is associated with the mite bodies; see Batard el al. Int Arch Allergy Immunol 2006, 140, p. 295-305.

As mentioned above there is a considerable batch to batch variation in the content of mite group 1 and mite group 2 allergens in batches of whole mite culture extracts, including extracts of mite bodies, which makes it very difficult to prepare mite extracts with a constant and predetermined level of group 1 and group 2 allergen. This is of course a serious problem in the industrial or large scale production of a pharmaceutical product which should contain as closely as possible the same amount of active ingredient(s) in every batch.

Therefore improved processes and product(s) are important to maximize production efficiency as well as provide high quality products for end-user efficacy and safety.

SUMMARY OF THE INVENTION

Accordingly, the present invention relates to a pharmaceutical product comprising an allergen extract or an allergoid thereof, which comprises at least one extract of mite bodies selected from the following groups a)-b):
  a) An extract of Der p mite bodies,
  b) An extract of Der f mite bodies,
  and at least one extract of mite cultures selected from the following groups c)-g):
  c) An extract of Der p faecal particles,
  d) An extract of Der f faecal particles,
  e) An extract of Der f whole mite culture,
  f) An extract of an Der p whole mite culture,
  g) a combination of extracts c) to f).

The present invention also relates to a pharmaceutical product comprising an allergen extract or an allergoid thereof, which comprises at least one extract of mite bodies selected from the following groups a)-b):
  a) An extract of Der p mite bodies,
  b) An extract of Der f mite bodies,
  and at least one extract of mite faecal particles selected from the following groups c)-d):
  c) An extract of Der p faecal particles,
  d) An extract of Der f faecal particles.

The invention also relates to a mite body fraction comprising more than 70% v/v mite bodies, more preferred more than 75% v/v mite bodies, more preferred more than 80% v/v mite bodies, preferably more than 85% v/v mite bodies, preferably more than 90% v/v mite bodies, preferred more than 95% v/v mite bodies and most preferred more than 98% v/v mite bodies.

The invention also relates to a mite faecal particle fraction comprising more than 70% v/v faecal particles, preferably more than 75% v/v faecal particles, preferably more than 80% v/v faecal particles, preferably more than 85% v/v faecal particles, preferably more than 90% v/v faecal particles, more preferred more than 95% v/v faecal particles, most preferred more than 98% v/v faecal particles.

The invention also relates to a method for the manufacture of a mite allergen extract comprising Der p 1 and Der p 2 allergen, which method comprises the following steps:
  a) Isolating fraction(s) of Der p mite bodies from cultures of Der p mites, where said fraction(s) comprises more than 70% v/v Der p mite bodies, more preferred more than 75% v/v Der p mite bodies, more preferred more than 80% v/v Der p mite bodies, preferably more than 85% v/v Der p mite bodies, preferably more than 90% v/v Der p mite bodies, preferred more than 95% v/v Der p mite bodies and most preferred more than 98% v/v Der p mite bodies;
  b) Optionally combining several of said fraction(s) of Der p mite bodies; and
  c) Extracting allergens from said Der p mite body fraction(s) obtained in a step a) or a step b) as above to obtain said mite allergen extract.

The invention also relates to a method for the manufacture of a mite allergen extract comprising Der f 1 and Der f 2 allergens, which method comprises the following steps:
  a) Isolating fraction(s) of Der f mite bodies from cultures of Der f mites, where said fraction(s) comprises more than 70% v/v Der f mite bodies, more preferred more than 75% v/v Der f mite bodies, more preferred more than 80% v/v Der f mite bodies, preferably more than 85% v/v Der f mite bodies, preferably more than 90% v/v Der f mite bodies, preferred more than 95% v/v Der f mite bodies and most preferred more than 98% v/v Der f mite bodies;
  b) Optionally combining several of said fraction(s) of Der f mite bodies; and
  c) Extracting allergens from said Der f mite body fraction(s) obtained in a step a) or a step b) as above to obtain said mite allergen extract.

The invention also relates to a method for the manufacture of a pharmaceutical composition for the treatment and/or prevention of allergy or allergic asthma caused by house dust mites which comprise an allergen extract or allergoids thereof having a predetermined and controlled content of allergens selected from Der f 1, Der f 2, Der p 1 and Der p 2 allergens and comprising the following steps:
  a) Fractions of Der p mite bodies and/or fractions of Der p mite faecal particles are isolated from Der p cultures of mites, and/or fractions of Der f mite bodies and/or fractions of Der f mite faecal particles are isolated from Der f mite cultures; optionally
  b) Combining several fractions of Der p mite bodies, optionally combining several fractions of Der p faecal particles, optionally combining several fractions of Der f mite bodies and optionally combining several fractions of Der f faecal particles;
  c) Extracting allergens from mite body faction(s) obtained in a step a) or a step b) as above and/or extraction of allergens from mite faecal particle fraction(s) obtained in a step a) or a step b) as above; and thereafter d) Measuring the concentration (w/v) of group 1 and group 2 allergen in mite allergen extracts obtained in a step c) as above; and optionally e) mixing one or more extract(s) of mite bodies with one or more extract(s) of faecal particles as obtained in a step c) as above to obtain a mixture of allergen extracts with a predetermined concentration (w/v) of group 1 to group 2 allergen, and optionally f) converting the extract to allergoids of extract.

The invention also relates to an allergen extract of a series of allergen extracts for the use in a pharmaceutical allergen product for the treatment and/or prevention of allergy and allergic asthma caused by house dust mites, each allergen extract comprising at least one extract of mite bodies, and at least one extract of mite faecal particles, or a mite body extract from a fraction of mite bodies having less than 70% v/v mite bodies or an whole mite culture extract, wherein said allergen extract has a predetermined ratio of group 1 and group 2 allergen, and wherein the variance coefficient of said ratio is no more than 25, 20, 15, 10, or 7.5% for the series of extracts.

The invention also relates to an allergen extract of an series of allergen extracts for the use in a pharmaceutical allergen product for the diagnosis of allergy caused by house dust mites, each allergen extract comprising at least one extract of mite bodies and at least one extract of mite faecal particles, or a mite body extract from a fraction of mite bodies having less than 70% v/v mite bodies or an whole mite culture extract, wherein said allergen extract has a predetermined ratio of group 1 and group 2 allergen, and wherein the variance coefficient of said ratio is no more than 25, 20, 15, 10, or 7.5% for the series of extracts.

BRIEF DESCRIPTION OF THE FIGURES

FIG. 1 shows a set-up as further described in Example 2.

DEFINITIONS

As used herein "mite" refers to house dust mites. Examples of such mites are *Dermatophagoides farinae* and/or *Dermatophagoides pteronyssinus* and/or *Euroglyphus maynei* or other important species belonging to the family of Pyroglyphidae.

As used herein "Der p" means "*Dermatophagoides pteronyssinus*", "Der p 1" means "group 1 allergen of Der p" and "Der p 2" means "group 2 allergen of Der p".

As used herein "Der f" means "*Dermatophagoides farinae*", "Der f 1" means "group 1 allergen of Der f" and "Der f 2" means "group 2 allergen of Der f".

The group 1 allergens and the group 2 allergens of the two mite species Der f and Der p exist naturally in a number of isoforms, see e.g. www.allergen.org under allergen sources (*Animalia Anthropoda/Astigmata/Dermatophagoides farinae* or *Dermatophagoides farinae*). As used herein "group 1 allergen", "group 1", "group 2 allergen" and "group 2" includes all naturally occurring isoforms of each of the group 1 and group 2 allergens including those mentioned on www.allergen.org.

As used herein "culture of mites" or "mite culture", "whole mite culture" and "whole culture", "Der p mite culture" and "Der f mite culture" or "cultures of Der p mites" and "cultures of Der f mites" means the material obtained after growth of Der p or Der f on a suitable medium and contains the whole culture including mites, parts of mites, faecal particles, eggs, mite media components etc.

As use herein "mite culture media or medium" or "mite media or medium" means a diet suitable for growing house dust mites.

As used herein "extract of mite bodies", "extract of Der p mite bodies" and "extract of Der f mite bodies" means "extract of one fraction or more combined fractions of mite bodies", "extract of one fraction or more combined fractions of Der p mite bodies" and "extract of one fraction or more combined fractions of Der f mite bodies" respectively.

As used herein "extract of mite faecal particles", "extract of faecal particles", "an extract of Der p faecal particles" and "extract of Der f faecal particles" means "extract of one or more combined fraction(s) of mite faecal particles", "extract of one fraction or more combined fraction(s) of faecal particles", "extract of one or more combined fraction(s) of Der p faecal particles" and "extract of one or more combined fraction(s) of Der f faecal particles", respectively.

As used herein "allergen extract" and "allergen extract (I)" are used interchangeably and mean an extract of at least one "mite body extract" or "faecal particle extract" optionally in combined with further mite extracts and in any combination.

As used herein "fraction(s) of mite bodies", means one or more combined fraction(s) of mite cultures that contain more than 50% v/v mite bodies, "fraction(s) of Der p mite bodies" means one or more combined fraction(s) of mite Der p cultures that contain more than 50% v/v Der p mite bodies, and "fraction(s) of Der f bodies" means one or more combined fraction(s) of Der f mite cultures that contain more than 50% v/v Der f bodies.

As used herein "fraction(s) of mite faecal particles" and "fraction(s) of faecal particles", means one or more combined fraction(s) of mite cultures that contain more than 50% v/v mite faecal particles, "fraction(s) of Der p faecal particles" means one or more combined fraction(s) of Der p mite cultures that contain more than 50% v/v Der p faecal particles, and "fraction(s) of Der f faecal particles" means one or more combined fraction(s) of Der f mite cultures that contain more than 50% v/v Der f faecal particles.

As used herein "(s)" as the last part of a word means the word in either singular or plural form.

As used herein "treatment" means "curing or alleviation of allergic symptoms".

As used herein "fast dissolving sublingual tablet" refers to compressed and non-compressed dosage forms which disintegrate in less than about 90 seconds, preferably in less than about 60 seconds, preferably in less than about 30 seconds, more preferably in less than about 20, even more preferably in less than about 10 seconds in the oral cavity, even more preferred in less than about 5 seconds, and most preferably in less than about 2 seconds after being received under the tongue in the oral cavity. Such fast dissolving sublingual tablets are described in e.g. WO 04/77994.

As used herein "CV" shall mean the coefficient of variation expressed in percentage.

DETAILED DESCRIPTION OF THE INVENTION

The pharmaceutical products of the invention are suitable for the treatment and/or prevention of house dust mite allergy and allergic asthma caused by house dust mites.

As mentioned above there is a considerable batch to batch variation in the content of mite group 1 and mite group 2 allergens in batches of whole mite culture extracts, including extracts of mite bodies, which makes it very difficult to prepare mite extracts with a constant and predetermined level of group 1 and group 2 allergen.

It has now been found that by preparing several, such as two extracts, for each batch of mite culture, for example by isolating a fraction of the mite culture containing primarily mite bodies and a fraction of the mite culture comprising mainly mite faecal particles followed by separate extraction of the mite body fraction and the mite faecal particles fraction provides the ability to control of the ratio of group 1 to group 2 allergen in the final allergen extract by mixing the mite body extract with mite faecal particles extract until the desired weight ratio is reached.

It has also been found that if the mite culture obtained by cultivation of mites is purified to produce a mite body fraction containing more than 70% v/v or more preferred more than 80% v/v, more preferred more than 85% v/v, more preferred more than 90% v/v, more preferred more than 95% v/v or more preferred more than 98% v/v mite bodies, extraction of this purified mite body fraction will normally produce a mite body extract which contain equal amount by weight of group 1 and group 2 allergen or more group 2 allergen than group 1 allergen.

A mite body extract with more group 2 than group 1 allergen by weight may be supplemented with extract of mite faecal particles which normally contain more group 1 allergen than group 2 allergen by weight to create a mixture of extracts with predetermined and if desired more equal amounts by weight of group 1 and group 2 allergen.

Examples of extracts, which normally contain more group 1 allergen than group 2 allergen by weight and which may be used to supplement with, is an extract of a whole mite culture or a body fraction(s) having less than 70% v/v of mite bodies.

A mite body extract with more group 2 than group 1 allergen by weight may also be supplemented with extract of whole mite culture or a mite body fraction having less than 70 v/v ° A) mite bodies, both which normally contain more group 1 allergen than group 2 allergen by weight to create a mixture of extracts with predetermined and if desired more equal amounts by weight of group 1 and group 2 allergen.

It is possible by mixing extracts of mite bodies and other fractions, preferably faecal particles fractions to obtain a mixture of extracts which contain a broad range of group 1 to group 2 weight ratios, such as from 1:0.6 to 1:1.6, 1:0.7 to 1:1.5, 1:0.8 to 1:1.4, 1:0.9 to 1:1.3, 1:0.95 to 1:1.2, 1:0.98 to 1:1.15, including a mixture which contain equal amounts by weight of group 1 and group 2 allergens, i.e. a 1:1:1:1 mixture of Der p 1, Der p 2, Der f 1 and Der f 2.

In one aspect, the invention relates to a method for the manufacture of a mixture of mite allergen extracts for a pharmaceutical product having a predetermined, controlled amount by weight of Der f 1, Der f 2, Der p 1 and Der p 2 allergens.

The invention also relates to a pharmaceutical product comprising allergen extracts selected from at least one extract of mite bodies and optionally at least one extract of mite faecal particles selected from: a) an extract of Der p mite bodies, b) an extract of Der p faecal particles, c) an extract of Der f mite bodies, and d) an extract of Der f faecal particles where the major allergens Der p 1, Der p 2, Der f 1 and/or Der f 2 is present in predetermined, controlled amounts.

In some embodiments the extracts of the invention are characterized by containing more group 2 allergen by weight compared to products on the market. The inventors of the present application have provided an industrial or large scale process for producing mite allergen extracts with this altered weight ratio between group 1 and group 2 allergen.

It has been found that if separate extracts of both mite bodies and mite faecal particles are prepared for each of the two mite species, and a sufficiently pure mite body fraction (and mite faecal particles fraction) is used for extraction it is possible to create mite extracts with a weight ratio of group 1 to group 2 allergen that is between 1:0.6 to 1:1.6 for each mites species.

By combining the extracts of both species a weight ratio between Der p 1, Der p 2, Der f 1 and Der f 2 that is 1:1:1:1 may be achieved.

These products are advantageous because the content of allergens in the pharmaceutical products is well controlled.

Previously mite allergen extracts typically contained more group 1 allergen than group 2 allergen by weight which may have caused a poor treatment of allergic patients that are particularly sensitized to group 2 allergen.

According to the invention, an industrial process for the preparation of extracts with a higher amount by weight of group 2 allergen than group 1 allergen than normally found in extracts have been provided.

Suitably, the pharmaceutical product as above comprises at least one extract of mite bodies and at least one extract of mite faecal particles selected from the groups a)-d) above.

Preferably the mite allergen extract comprises an extract of Der p mite bodies, an extract of Der p faecal particles, an extract of Der f mite bodies and an extract of Der f faecal particles.

According to further embodiments of the invention the mite allergen extract comprise:

- An extract of Der p mite bodies and an extract of Der p faecal particles and optionally no extracts of Der f mite bodies and no extracts of Der f faecal particles; or
- An extract of Der f mite bodies and an extract of Der f faecal particles and optionally no extracts of Der p mite bodies and no extracts of Der p faecal particles; or
- An extract of Der p mite bodies and an extract of Der f mite bodies and optionally no extract of mite faecal particles; or
- An extract of Der p mite bodies and no extract of Der f mite bodies and optionally no extract of mite faecal particles; or
- An extract of Der f mite bodies and no an extract of Der p mite bodies extract and optionally no extract of mite faecal particles.

In a preferred embodiment of the invention the extract of Der p mite bodies is prepared from one or more fraction(s) of Der p mite bodies where extraction of the fraction(s) of Der p mite bodies results in an extract comprises equal amounts by weight of group 1 and group 2 allergen or more group 2 allergen than group 1 allergen by weight and/or the extract of Der f mite bodies is prepared from one or more fraction(s) of Der f mite bodies and where extraction of the fraction(s) of Der f mite bodies results in an extract comprises equal amounts by weight of group 1 and group 2 allergen or more group 2 allergen than group 1 allergen by weight.

In a preferred embodiment

- the extract of Der p mite bodies is suitably prepared from one fraction or combined fractions of Der p mite cultures said fraction(s) comprising more than 70% v/v Der p mite bodies, more preferred more than 75% v/v Der p mite bodies, more preferred more than 80% v/v Der p mite bodies, preferably more than 85% v/v Der p mite bodies, preferably more than 90% v/v Der p mite bodies, preferred more than 95% v/v Der p mite bodies and most preferred more than 98% v/v Der p mite bodies, and/or
- the extract of Der f mite bodies is suitably prepared from one fraction or combined fractions of mite Der f cultures said fractions comprising more than 70% v/v Der f mite bodies, preferably more than 75% v/v Der f mite bodies, preferably more than 80% v/v Der f mite bodies, preferably more than 85% v/v Der f mite bodies, preferably more than 90% v/v Der f mite bodies, more preferred more than 95% v/v Der f mite bodies, and preferably more than 98° A) v/v Der f mite bodies, and/or the extract of Der p faecal particles is suitably prepared from one fraction or combined fraction(s) of Der p mite cultures said fraction(s) comprising more than 70% v/v Der p faecal particles, preferably more than 75% v/v Der p faecal particles, preferably more than 80% v/v Der p faecal particles, preferably more than 85% v/v Der p faecal particles, preferably more than 90% v/v Der p faecal particles, more preferred more than 95% v/v Der p faecal particles, most preferred more than 98% v/v Der p faecal particles and/or the extract of Der f faecal particles is suitably prepared from one fraction or combined fraction(s) of Der f mite cultures said fraction(s) comprising more than 70% v/v Der f faecal particles, preferred more than 75% v/v Der f faecal particles, preferred more than 80% v/v Der f faecal particles, preferably more than 85% v/v Der f faecal particles, preferably more than 90% v/v Der f faecal particles, preferred more than 95% v/v, and more preferred more than 98% v/v Der f faecal particles.

In one embodiment of the invention, the faecal fraction is not so pure as the body fraction.

In a preferred embodiment each of the fractions or combined fractions above comprises below 10% v/v mite culture media particles.

The mite body fraction or combined mite body fractions may contain up to 20% v/v mite parts (legs, eggs etc), medium and faecal particles (i.e. anything that is not mite bodies or contaminants), provided the amount of medium particles is below 10% v/v.

The mite faecal particles fraction or combined mite faecal particles fractions may contain up to 20% v/v mite parts (legs, eggs etc) and media particles (i.e. anything that is not faecal particles or contaminants), provided the amount media particles is below 10% v/v.

In a further embodiment each of the fractions or combined fractions is comprised of no more than a total of 1.0% w/w of detectable foreign materials. Mite faecal particles, mite parts, mite bodies or mite media are not considered to be foreign materials.

The volumetric percentages of mite bodies and mite faecal particles in the mite body and faecal fractions of particles are determined by microscopy. The number of particles (e.g. mite body or faecal particle) is counted and expressed as % v/v by multiplication with a figure which is the average volume for the particle in question (e.g. mite body or faecal particle).

Microscopic Count Performed on Mite Body Fractions:

A sample is weighed out and suspended in a glycerol containing solution (25% glycerol, 5% Igepal). The sample is poured onto a gridded filter while under vacuum in order to remove the liquid and immobilise the particles on the filter. The filter is then dried to increase visibility when using the microscope. Grids to be counted are chosen at random and all particles within a chosen grid are counted. Grids are chosen until at least 800 particles have been counted. The above procedure may be performed on several such as two, three, four or five independent samples. When calculating the results, the variation between the samples has to meet a desired acceptance criteria (such as for example more than 80 vol/vol % whole mite bodies, and/or less than 10 vol/vol % media particles) for the assay in order to ensure consistency between the samples. If the results from the samples are consistent, then the counts are averaged giving the assay result.

The non-volumetric counts are translated into volumes by using predetermined assigned volumes for mite bodies, faecals, and medium particles.

Microscopic Count Performed on Faecal Fractions:

A sample is weighed out, placed in a gridded counting chamber and mixed with paraffin oil to give an even layer. Grids to be counted are chosen at random and all particles within a chosen grid are counted. Grids are chosen until at least 800 particles have been counted. The above procedure may be performed on several such as two, three, four or five independent samples. When calculating the results, the variation between the samples has to meet an acceptance criteria (such as for example more than 80 vol/vol % whole mite bodies, and/or less than 10 vol/vol % media particles) for the assay in order to ensure consistency between the samples. If the results from the samples are consistent, then the counts are averaged giving the assay result The non-volumetric counts are translated into volumes by using predetermined assigned volumes for mite bodies, faecals, and medium particles.

The volumes assigned to mite bodies, faecal particles, mite medium particles are as follows:

Der f mite bodies: 21132000 cubed micrometers
Der p mite bodies: 12926000 cubed micrometers
Mite medium particles in body fractions: 6721000 cubic micrometers
Mite medium particles in faecal fractions: 10000 cubic micrometers
Faecal particles: 19000 cubic micrometers As mentioned above the present invention is based on the finding that by purifying the mite body fraction(s) so that they contain more than 70% v/v of mite bodies, more preferred more than 80% v/v, more preferred more than 85% v/v, more preferred more than 90% v/v, more preferred more than 95% v/v or more preferred more than 98% v/v it is possible to prepare a mite body extract from such mite body fraction or combined fractions where the amount by weight of group 1 allergen in the extract is lower than the amount of group 2 allergen by weight or the concentration of group 1 and group 2 allergen by weight is equal.

According to a preferred embodiment, the amount by weight of group 1 allergen is lower than the amount by weight of group 2 allergen in the mite body extract(s) and the amount by weight of group 1 allergen is much higher than the weight group 2 allergen in the extracts of mite faecal particles.

Suitably the weight ratio of group 1 to group 2 allergen in the allergen extract is closer to the weight ratio of group 1 allergen to group 2 allergen in the mite body extracts than the weight ratio of group 1 to group 2 allergen in the mite faecal particles extracts which is used for the preparation thereof.

According to the invention it is possible to alter the weight ratio of group 1 to group 2 allergen to more equal amounts by weight in the extract, than in the extract of mite bodies and mite faecal particles from which they were prepared. This was not possible previously where typical batches of both mite bodies and the faecal particles contain more group 1 allergen than group 2 allergen by weight.

A pharmaceutical product of the invention is provided, comprising allergen extract, which comprises allergens selected from Der f 1, Der f 2, Der p 1 and Der p 2 and where the allergen present in the lowest concentration (w/v) in the allergen extract, is present in a concentration which is above 50% of the concentration of the allergen selected from Der f 1, Der f 2, Der p 1 and Der p 2 present in the highest concentration (w/v), more preferred above 60% of the concentration of the allergen selected from Der f 1, Der f 2, Der p 1 and Der p 2 present in the highest concentration (w/v), more preferred above 70% of the concentration of the allergen selected from Der f 1, Der f 2, Der p 1 and Der p 2 present in the highest concentration (w/v), more preferred above 80% of the concentration of the allergen selected from Der f 1, Der f 2, Der p 1 and Der p 2 present in the highest concentration (w/v), more preferred above 85% of the concentration of the allergen selected from Der f 1, Der f 2, Der p 1 and Der p 2 present in the highest concentration (w/v), more preferred above 90% of the concentration of the allergen selected from Der f 1, Der f 2, Der p 1 and Der p 2 present in the highest concentration (w/v), more preferred above 95% of the concentration of the allergen selected from Der f 1, Der f 2, Der p 1 and Der p 2 present in the highest concentration (w/v), preferred above 98% of the concentration of the allergen selected from Der f 1, Der f 2, Der p 1 and Der p 2 present in the highest concentration (w/v), or most preferred above 99% of the concentration of the allergen selected from Der f 1, Der f 2, Der p 1 and Der p 2 present in the highest concentration (w/v).

One daily dose of a product of the invention suitably contain from 1-25 µg or more, 1-15 µg or more, 1-12 µg or more, 1-10 µg or more, 2 to 10 µg or more preferred from 3 to 8 µg Der p 1, from 3 to 8 µg Der p 2, from 3 to 8 µg Der f 1 and from 3 to 8 µg Der f 2.

In a preferred embodiment the daily dose of group 1 and group 2 allergens in a sublingual product of the invention is suitably between 3 and 4 µg, more preferred around 3.6 µg of Der p 1, Der p 2, Der f 1 and/or Der f 2.

In another embodiment the daily dose of group 1 and group 2 allergens in a sublingual product of the invention suitably between 6 and 8 µg, more preferred around 7.2 µg of Der p 1, Der p 2, Der f 1 and/or Der f 2.

The pharmaceutical product as above may be formulated as a compressed or non-compressed sublingual tablet (e.g. as in WO 04/77994), a liquid sublingual product (e.g. as in WO 07/051476) or a liquid product for injection optionally adjuvanted with aluminium hydroxide (e.g. as in WO 10/043675). Preferably the pharmaceutical product is a fast dissolving, sublingual tablet. Suitably the tablets are in the form of tablets, capsules, lozenges or caplets.

The allergen extract may be present in the form of allergoids in the pharmaceutical products described above.

The present invention also relates to a method for the manufacture of a mite allergen extract for a pharmaceutical product said extract having a predetermined, controlled and if desired a more equal weight ratio of Der f 1, Der f 2, Der p 1 and/or Der p 2 allergen.

The invention also relates to a method for the manufacture of a mite allergen extract or allergoids thereof for a pharmaceutical product as described above wherein said allergen extract having a predetermined and controlled amount by weight of allergens selected from Der f 1, Der f 2, Der p 1 and Der p 2 allergens and comprising the following steps a), and c)-d) and optionally b), e) and/or f):

a) Fractions of Der p mite bodies and/or fractions of Der p mite faecal particles are isolated from Der p cultures of mites, and/or fractions of Der f mite bodies and/or fractions of Der f mite faecal particles are isolated from Der f mite cultures;

b) Optionally combining several fractions of Der p mite bodies, optionally combining several fractions of Der p mite faecal particles, optionally combining several fractions of Der f mite bodies and optionally combining several fractions of Der f mite faecal particles;

c) Extracting allergens from mite body fraction(s) obtained in a step a) or a step b) as above and/or extraction of allergens from faecal particle fraction(s) obtained in a step a) or a step b) as above; and thereafter d) Measuring the concentration (w/v) of group 1 and group 2 allergen in mite allergen extracts obtained in a step c) as above; and optionally e) Mixing one or more extract(s) of mite bodies with one or more extract(s) of mite faecal particles as obtained in a step c) as above to obtain a mixture of allergen extracts with a predetermined amount and weight ratio of group 1 to group 2 allergen, and optionally f) Converting the allergen extract to an allergoid thereof.

According to the invention extracts of fractions of mite bodies and extracts of fractions of mite faecal particles may be combined or mixed, however fraction(s) of mite bodies are never combined with faecal particles fraction(s).

Suitably one or more extract(s) of mite bodies and one or more extract(s) of faecal particles are mixed to obtain a mixture of allergen extracts.

Preferably the mixture of mite allergen extract comprises extract(s) of Der p mite bodies, extract(s) of Der p faecal particles, extract(s) of Der f mite bodies and extract(s) of Der f 2 faecal particles.

To prepare the extract more than one fraction of mite bodies may be combined according to step b) followed by extraction according to step c).

Also more than one fraction of mite faecal particles may be combined according to step b) followed by extraction according to step c).

Alternatively, a fraction of mite bodies obtained in step a) is subjected to extraction and/or a fraction of mite faecal particles obtained in step a) is subjected to extraction.

Suitably one or more extract(s) of mite bodies obtained in a step c) is mixed in a step e) with one or more extract(s) of mite faecal particles obtained in a step c).

Suitably one extract of mite bodies obtained in a step c) is mixed in a step e) with one extract of mite faecal particles obtained in a step c).

In the method as above one or more extract(s) of mite bodies obtained in a step c) may be mixed in step e) with one extract of mite faecal particles obtained in a step c).

Alternatively, one extract of mite bodies obtained in a step c) may be mixed in a step e) with one or more extract(s) of mite faecal particles obtained in a step c).

As used herein, "mixing of extracts" include mixing of both whole batches of extracts as well as parts of whole batches.

According to a preferred embodiment of the invention the mite body extract(s) are supplemented with an amount of faecal particles extract which is sufficient to achieve the desired weight ratio of group 1 allergen to group 2 allergen in the mixture of mite allergen extracts.

In another preferred embodiment of the invention, the mite body extract already has an almost equal amount of group 1 and group 2 allergen by weight and need not be mixed with mite faecal particles extract.

The coefficient of variation (CV) is calculated as the ratio of the standard deviation $\sigma$ to the mean $\mu$:

$$c_v = \frac{\sigma}{|\mu|}$$

It is sometimes expressed as percentage, in which case the CV is multiplied by 100.

The CV is used to describe the improved batch-to batch consistency of the extract and pharmaceutical products (therapeutic or diagnostic) according to the invention. Confidence Intervals (CI) such 95% may be used.

It is sometimes expressed as percentage, in which case the CV is multiplied by 100.

The CV is used to describe the improved batch-to batch consistency of the extract and pharmaceutical products (therapeutic or diagnostic) according to the invention. Confidence Intervals (CI) such 95% may be used.

Cultivation of Mites:

A number of diets suitable for growth of the mites are known and there have been numerous studies of the effectiveness of different culture medium ingredients such as yeast, albumins, feed for animals, feed for fish (Tetramin), derivatives of shed human skin scales, pork skins, brine shrimp eggs, wheat germs, rat food, dog food, powdered animal liver, hydrolysate of milk proteins, vitamins, minerals, protein hydrolysate and soya flour.

Mite diets are for example described in International Journal of Acarology, Vol. 8, Issue 3 (1982), p. 189-192, Rodrigues, Recent Advances in Acarology, Vol. 11 (1979), 211-216, Batard et al., Int Arch Allergy Immunol. 140 (2006) p. 295-305, Yi et al.; Asian Pacific Journal of Allergy and Immunology, 17 (1999), p. 189-194, Arlian et al., J. Allergy. Clin. Immunol, No. 3 (1987), p. 457-66, and EP patent No. 1236394.

One example of a medium for rearing mites comprising a 1:1 mix of yeast and dried Daphnia is described in Dust Mites by Matthew Colloff (2009), p. 270. Another example of a medium for rearing mites is as described in EP patent No. 1236394.

It is preferred to use a protein hydrolysate as well as other ingredients that are of low allergenic risk in order to reduce the possibility of anaphylactic reactions in allergen sensitized patients. It is further preferred to use mite medium that do not contain animal or human protein.

Suitably the mite medium is used in the form of particles which are of sufficient size and integrity to withstand the rigors of downstream processing and be easily eliminated through the primary screening process.

The two mite species Der p and Der f are always grown in separate containers but may be grown on the same mite medium. Examples of containers include glass or plastic containers of suitable size and shape such as fly-bottles. Disposable containers for culturing mites are for example described in WO2008/119762.

The mites are cultivated in containers with culture medium and are placed in controlled environment controlling the temperature and humidity of the environment surrounding the growing mite cultures. Suitable conditions for Der p and Der f are for example described in a number of articles such as by Fain et al (ISBN 90-71868-12-5) and by Crowther: Exp Appl Acarol. 2007; 41(1-2):61-86.

One suitable set of parameters for the cultivation conditions for each of the mite species is provided in table 1a below.

TABLE 1a

| | Der f | Der p |
|---|---|---|
| Relative humidity | 65% ± 5% RH | 70% ± 5% RH |
| Temperature | 25° C. ± 5° C. such as 27.5° C. ± 2° C. | 25° C. ± 7° C. such as 30° C. ± 2° C. |
| Cultivation time | 42-70 such as 42-56 days | 42-70 such as 42-56 days |

Microscopic counts for growth and viability are performed during the cultivation or order to identify the optimal time for harvesting the mites.

Killing of the culture may be performed by freezing. Mites can also be killed by e.g. suffocation with e.g. acetone. Storage containers with killed mite culture are stored at −20° C. until further processing.

Purification of Mite Culture:

The mite cultures are thawed and dried and sieved to obtain fractions of the mite culture containing components of different sizes. Drying may be carried out by airflow until moisture is less than 20%, more preferred 15%

The mite culture may be further purified and mite body or faecal fractions isolated using separation techniques including sieving (e.g. using meshes of 1 mm, 500 µm, 250 µm, 100 µm on a sieve-shaker), saturated sodium chloride suspensions, and ethanol suspension, see e.g. Dust Mites by Matthew Colloff (2009), p. 271.

In one embodiment the fraction(s) of mite bodies and the fraction(s) of mite faecal particles may be prepared by sieving of the mite culture to produce four fractions:
a) Large medium particles>350 µm
b) Mite body fraction 350-90 µm
c) Faecal agglomerates and mite parts 90-50 µm
d) Faecal particles<50 µm It is within these size ranges the different components of the mite culture, such as the mite bodies, the faecal particles and medium particles etc. are usually found. Mite culture fractions isolated within a size range that differ from the size ranges above may also be useful according to the invention as long as it is possible to prepare mite body fractions and faecal particles that are sufficiently pure and in sufficient amount.

Fraction a) and c) are discarded. Fraction d) may be used directly in the extraction process and fraction b) is subjected to further purification before extraction.

Purification of Mite Body Fraction:

A method for purification of mite bodies from medium particles by flotation in a suitable liquid have been described previously, GB patent no. 1318560 on page 3. J. Med. Entomol. (1979), Vol. 16, No. 2, p. 128-132 describes flotation in alcohol (ethanol) for the separation of mite bodies from mite media particles.

It has now been found that density centrifugation, optionally repeated, of the mite body fraction in a suitable liquid produces a mite body fraction of high purity which when extracted produces an extract with more group 2 allergen than group 1 allergen weight, or an equal amount by weight of group 1 and group 2 allergen.

Thus the present invention also relates to a method for the isolation and purification of mite bodies comprising the steps:

i) Isolating mite body fraction(s) from Der p and/or Der f mite culture(s) and ii) Subjecting one or more Der p mite body fraction(s), or one or more Der f mite body fraction(s), to density centrifugation in a first liquid medium having a higher density than the mite bodies and a lower density than the culture media at the temperature used during the centrifugation; and iii) Collecting the mite bodies from the surface of said first liquid medium and optionally repeating step ii) and iii) until the desired purity of the mite bodies have been achieved, optionally followed by iv) Washing of the mite bodies to remove said first liquid with a second liquid that does not extract group 1 and group 2 allergen from the mite bodies at the temperature used during the washing step.

The present invention also relates to a method for the isolation and purification of mite bodies comprising the steps:

i) Isolating mite body fraction(s) from Der p and/or Der f mite culture(s) and ii) Subjecting one or more Der p mite body fraction(s), or one or more Der f mite body fraction(s), to density centrifugation in a first liquid medium having a higher density than the mite bodies and a lower density than the culture media at the temperature used during the centrifugation; and iii) Collecting the mite bodies from the surface of said first liquid medium optionally followed by iv) Washing of the mite bodies to remove said first liquid with a second liquid that does not extract group 1 and group 2 allergen from the mite bodies at the temperature used during the washing step.

Centrifugation parameter settings e.g. Relative Centrifugation Force (RCF), velocity (RPM; Round Per Minutes), centrifugation time, rates of liquid to mite body fraction(s), temperature are well known to the skilled person in the art and may have to be adjusted depending on centrifugation equipment and degree of automation. Useful RCF are in range of 500-5000 RCF. Setting include 1000-7000 RPM and centrifugation time of 1-20 minutes or more preferred 1500-6000 RPM and 2-15 minutes, even more preferred 2000-4000 and 3-12 minutes. Centrifugation cups may be filled or filled less. The rate of dried mite fraction to liquid (w/w) varies depending on liquid used. Preferably the amount of liquid (weight) used for centrifugation exceeds the amount (weight) of the mite body fraction by more than a factor 1, more preferably by a factor 3, even more preferred by a factor 5 or above.

Preferably the first and second liquid in the process above does not contain water (anhydrous) to limit the extraction of allergens from the source material in the instant source material purification step. In another embodiment, the method for the isolation and purification of mite bodies the step ii) of subjecting one or more Der p mite body fraction(s), or one or more Der f mite body fraction(s), to density centrifugation in a first liquid medium is performed with a first liquid having iia) a higher density than the mite bodies and a lower density than the culture media particles and iib) do not extract group 1 and group 2 allergen form the mite bodies at the temperature used during the centrifugation.

Suitable liquids comprise metrizoic acid derivatives (like iohexol, Nycodenz® (N-2,3-dihydroxypropylacetamido-2,4, 6-tri-iodo-N—N-bis(2,3-dihydroxypropyl)), polypropyleneglycols (such as ARCOL® (polypropyleneglycol 4000), Silica based compositions (like RediGrad®).

It is difficult to completely avoid some extraction of group 1 and group 2 allergen from the mite bodies during the centrifugation process above. According to the invention, liquids that do not extract group 1 and group 2 allergens from the mite bodies are liquids that do not extract group 1 allergen and group 2 allergen from the mite bodies at the temperature used in step ii) and iv) above in an amount that seriously affect the final yield and ratio of group 1 and group 2 allergen.

Extraction of group 1 and group 2 allergen from the mite bodies during the centrifugation process may be reduced by carrying out the centrifugation at a low temperature e.g. freezing temperature.

In a preferred embodiment the liquid having a density higher than the mite bodies and lower than the culture media particles is an anhydrous liquid, for example anhydrous glycerol.

The glycerol may be removed from the mite bodies by washing with ethanol, preferably anhydrous ethanol.

Suitable step ii) and iii) are repeated once or the centrifugation in glycerol is repeated until the mite body fraction obtained is composed of at least 70% v/v mite bodies, more preferred more than 75% v/v mite bodies, more preferred more than 80% v/v mite bodies, preferably more than 85% v/v mite bodies, preferably more than 90% v/v mite bodies, preferred more than 95% v/v mite bodies and most preferred more than 98% v/v mite bodies and the mite body fraction contain below 20% v/v mite parts, faecal particles and medium particles and below 10% v/v medium particles.

Instead of density centrifugation with glycerol as describe in step ii) and iii) the mite body fraction may be purified by separation with saturated NaCl as the first liquid until the mite body fraction is composed of at least 70% v/v mite bodies, more preferred more than 75% v/v mite bodies, more preferred more than 80% v/v mite bodies, preferably more than 85% v/v mite bodies, preferably more than 90% v/v mite bodies, preferred more than 95% v/v mite bodies and most preferred more than 98% v/v mite bodies and contain below 20% v/v mite parts, faecal particles and medium particles and below 10% v/v medium particles without the need for applying step iv).

Instead of density centrifugation the mite body fraction may be purified by sieving until the mite body fraction is composed of at least 70% v/v mite bodies, more preferred more than 75% v/v mite bodies, more preferred more than 80% v/v mite bodies, preferably more than 85% v/v mite bodies, preferably more than 90% v/v mite bodies, preferred more than 95% v/v mite bodies and most preferred more than 98% v/v mite bodies and contain below 20% v/v mite parts, faecal particles and medium particles and below 10% v/v medium particles.

Mite bodies may in one dimension be more than 400 μm long but may nevertheless be able to pass through a 300 μm and 400 μm sieve when they are dried before sieving.

Mite bodies have legs and hair and may be separated from mite media particles in sieve shaker with a horizontal circular movement. The method takes advantage of the mites ability to form tangles formed with their hair and legs when moved horizontally on a sieve. In a sieving tower which is moved horizontally in circles the mite bodies is captured on top of the 200, 300 and/or the 400 μm mesh sieves and is in this way separated from other mite culture particles with a size between 150 and 300 μm.

Thus, in an alternative to the centrifugation method the mite body rich fraction between 90 and 350 μm isolated in the sieving process above may be purified by the following method:

1) sieving Der f or Der p mite cultures in a vibrating sieve shaker with a tower of a 300, a 150 and a 80 μm mesh sieve followed by isolation of a mite body rich fraction between 150 μm and 300 μm and a mite faecal particles rich fraction below 80 μm, followed by 2) sieving the mite body rich fraction (150 μm and 300 μm) in a sieve shaker with a horizontally and circular movement and with a tower of 200, 300 and/or 400 μm mesh sieves and isolating body rich fraction(s) captured by the 200, 300 and/or 400 μm mesh sieves, followed by 3) sieving of the body rich fraction in a sieve shaker having a 3D throwing motion and 300, 200, 150 and 100 mesh sieve to produce a mite fraction between 150 and 300 μm mesh and a mite faecal particles extract below 100 μm; and optionally combining the faecal particles fraction below 80 μm from the vibrating sieve and the faecal particles fraction below 100 μm from the sieve with the 3D throwing motion and subjecting the combined faecal fraction to sieving in the sieve with the 3D throwing motion and a tower of 100, 80, 50 μm mesh sieves.

Mite body fractions b) obtained above may also be purified by steps 2 and 3 in the above process.

Extraction

The fractions of mite bodies and mite faecal particles are extracted in more or less the same way but in separate processes because the optimal conditions for extraction of mite bodies is not the same as for mite faecal particles.

In order to extract allergens from the mite bodies and the faecal particles these, bodies need to be cracked to release the allergens. Cracking can be achieved by applying an external force to a slurry of mite bodies.

According to the invention it has been found that a high shear mixer is particularly effective to crack and release the allergens from mite bodies and faecal particles.

Thus, according to one embodiment of the invention the extraction of allergens is carried out by suspending the mite bodies or the mite faecal particles in a buffer with a high shear mixer (typically for 15 to 30 minutes) and then allowing the extraction to proceed without mixing (typically for 1-6 hours).

The release of allergens is different for mite bodies and faecal particles. The allergens in the faecal particles are extracted after 1 hour of extraction whereas at least 3 hours are needed to extract allergens from the mite bodies.

Buffers for extraction of mite allergens are well known in the art.

The allergenic source material (mite body and/or mite faecal particles) may for example be extracted using an extraction buffer comprising 0.15 M NaCl, 0.012 M $NaHCO_3$ and NaOH/HCl/water to adjust pH. The extraction is suitably carried out using a ratio between extraction buffer to allergenic source material of 1:10 (w/w) a pH of 7-8, a temperature between 4-12° C. and an extraction time of between 1-6 hours.

These extracts may be subjected to further purification before they are used in a pharmaceutical product.

The remaining insoluble material may for example be removed from the extract of mite faecal particles by centrifugation and clarification. The mite faecal particles extract may thereafter be subjected to ultrafiltration performed in three steps: First concentration by removal of water and other small molecules by tangential flow filtration, followed by diafiltration to remove small molecules and salts and thereafter dry matter adjustment.

The allergen extract may thereafter be clarified by clarification filtration.

Further purification of the mite bodies extracts suitably involves the following processes: Separation using diafiltration leaving insoluble matter on the membrane and continuously adding water to the extract on the other side of the membrane. The extract is thereafter subjected to ultra filtration and clarification as described above.

The extracts may be stabilized by forming frozen balls of extracts (cryogranules) as described in WO 05/058474.

The concentration of group 1 and group 2 allergen in the extracts of mite bodies and mite faecal particles may be measured by a number of methods conventionally used for the measurement of allergen content including for example ELISA, RID/SRID (Single Radial immunodiffusion) or by MS (mass spectrometry e.g. as described in WO 2007/031080) see also above.

The principle of the RID procedure is that proteins (antigens) applied in a circular well diffuse outwards forming a concentration gradient in an agarose gel containing the corresponding antibody. The antibody used in this procedure is mono-specific (i.e. raised against a specific antigen) and polyclonal making it possible to form precipitates of antigen-antibody complexes. The antibody is present in excess and diffusion of the antigen will continue until the equivalence point is reached and a ring of antigen-antibody precipitates is formed. Subsequently, the precipitation rings are stained. The area of the precipitate is measured and the concentration of antigen in unknown samples can now be interpolated from the calibration curve generated with a reference standard. The major allergen content is determined relative to the reference standard (see e.g Allergy Methods and Protocols, Jones and Lympany (2008), p. 138-141, p. 152-153 and p. 159-161).

Different sandwich-ELISA (enzyme linked immunosorbent assay) methods can be used for determination of the major allergen content in Der p and Der far. One for determination of Der f 1, one for determination of Der p 1 and one for determination of Der group 2, since the two group 2 major allergens are immunochemically identical.

Monoclonal antibodies specific for the major allergen (Der f 1, Der p 1, Der group 2) are adsorbed to the wells of a 96-well microtitre plate. The mAbs recognize epitopes on the major allergen and bind the allergen present in the sample. The bound antibody-antigen is washed and a peroxidase labelled rabbit anti-major allergen IgG antibody is added. By addition of enzyme substrate a colour reaction will develop, which is directly proportional to the content of bound major allergen. A standard curve is also analyzed in the analytical run and the major allergen activity is interpolated on the calibration curve. Further to the use of an internal standard, Center for Biologics Evaluation and Research under FDA use a competition ELISA as described in "Potency Limits for Standardized Dust Mite and Grass Allergen Vaccines: A revised protocol. 2000 (http://www.fda.gov/BiologicsBlood-Vaccines/GuidanceComplianceRegulatoryInformation/Guidan ces/Allergenics/ucm071931.htm) for the potency labelling of allergen products.

In another preferred embodiment the concentration of group 1 and group 2 allergen is measured by MS (mass spectrometry) as described in WO 2007/031080 using the following calibration standard peptides:

```
(Der p 1)
                                            SEQ ID NO: 1
TNACSINGNAPAEIDLR, (Der f 1)
                                            SEQ ID NO: 2
NSWDTTWGDSGYGYFQAGNNLMMIEQYPYVVIM, (Der p 2)
                                            SEQ ID NO: 3
VLVPGCHGSEPCIIHR, (Der f 2)
                                            SEQ ID NO: 4
GKPFTLEALFDANQNTK,
and (Der f 1)
                                            SEQ ID NO: 5
GIEYIQQNGVVEER
```

When the concentration of group 1 and group 2 allergen has been determined for a number of mite extracts, mite body extracts and faecal particles extracts are mixed to achieve the desired weight ratio between group 1 and group 2 allergen.

Determining which extract and the weight of said extracts to be mixed is an iterative process where the amounts by weight of the extracts from different batches to be used is determined and filled in the following formula for Der f until the desired ratio is reached:

Major allergen ratio=Total group 1/Total group $2=mf1\times Cf1grp1+mb1\times Cb1grp1+mf2\times Cf2grp1+\ldots/mf1\times Cf1grp2+mb1\times Cb1grp2+mf2\times Cf2grp2+$ Where mf1 is mass of the first Der f faecal particles extract used, mf2 is mass of the second Der f faecal extract used etc. . . . Cf1grp1 is concentration of group 1 allergen in mf1, Cf2grp1 is the concentration of group 1 allergen the second faecal extracts used, mb1 is the first mite body extract used and Cb1grp1 is the concentration of group 1 allergen in mb1. Cf1grp2 is the concentration of group 2 allergen in mf1, Cb1grp2 is allergen concentration in mb1 and Cf2grp2 is the concentration group 2 allergen in mf2 etc. . . . .

A similar formula for Der p is used to determine which and how much extract to mix to form an extract with the desired ratio of group 1 to group 2 allergen.

The individual extracts are thawed and mixed according to the formula above.

The mixture of allergen extracts may be stabilized and stored as frozen droplets as described in WO 05/0058474 or used directly in a formulation.

The extracts are normally subjected to other standardization processes involving a number of tests, e.g. a potency test, before they are release for formulation.

The mixture of mite allergen extracts may be use as the active ingredient in a solid dose formulation for sublingual administration as described in WO 04/77994.

Alternatively, the mixture of allergen extracts may be formulated as a liquid formulation for sublingual administration as drops. Such formulation typically comprises about 50% glycerol, NaCl and NaOH.

The mixture may also be formulated as a liquid formulation for subcutaneous injection. The extract may either be administered as an aqueous liquid formulation without adjuvants or with an adjuvant such as aluminum hydroxide.

Allergoids may be prepared by cross-linking extracts with a cross-linking agent which is typically an aldehyde, such as glutaraldehyde. Processes for preparation allergoids are known in the art.

Further embodiments according to the invention:

Embodiment 1

A pharmaceutical product comprising an allergen extract or an allergoid thereof, which comprises at least one extract of mite bodies selected from the following groups a)-b):
a) An extract of Der p mite bodies,
b) An extract of Der f mite bodies,
and at least one extract of mite cultures selected from the following groups c)-g):
c) An extract of Der p faecal particles,
d) An extract of Der f faecal particles,
e) An extract of Der f whole mite culture,
f) An extract of an Der p whole mite culture,
g) a combination of extracts c) to f).

Embodiment 2

A pharmaceutical product comprising an allergen extract or an allergoid thereof, which comprises at least one extract of mite bodies selected from the following groups a)-b):
a) An extract of Der p mite bodies,
b) An extract of Der f mite bodies,
and at least one extract of mite faecal particles selected from the following groups c)-d):
c) An extract of Der p faecal particles,
d) An extract of Der f faecal particles.

Embodiment 3

The pharmaceutical product according to any one of embodiments 1-2,
wherein the extract of Der p mite bodies is prepared from one fraction or combined fraction(s) of mite cultures said fraction(s) comprising more than 70% v/v Der p mite bodies, more preferred more than 75% v/v Der p mite bodies, more preferred more than 80% v/v Der p mite bodies, preferably more than 85% v/v Der p mite bodies, preferably more than 90% v/v Der p mite bodies, preferred more than 95% v/v Der p mite bodies and most preferred more than 98% v/v Der p mite bodies, and/or
the extract of Der f mite bodies is prepared from one fraction or combined fraction(s) of mite cultures said fractions comprising more than 70% v/v Der f mite bodies, preferably more than 75% v/v Der f mite bodies, preferably more than 80% v/v Der f mite bodies, preferably more than 85% v/v Der f mite bodies, preferably more than 90% v/v Der f mite bodies, more preferred more than 95% v/v Der f mite bodies, and preferably more than 98% v/v Der f mite bodies.

Embodiment 4

A pharmaceutical product comprising allergen extract, which comprises allergens selected from Der f 1, Der f 2, Der p 1 and Der p 2 and where the allergen present in the lowest concentration (w/v) in the allergen extract, is present in a concentration which is above 50% of the concentration of the allergen selected from Der f 1, Der f 2, Der p 1 and Der p 2 present in the highest concentration (w/v), more preferred above 60% of the concentration of the allergen selected from Der f 1, Der f 2, Der p 1 and Der p 2 present in the highest concentration (w/v), more preferred above 70% of the concentration of the allergen selected from Der f 1, Der f 2, Der p 1 and Der p 2 present in the highest concentration (w/v), more preferred above 80% of the concentration of the allergen selected from Der f 1, Der f 2, Der p 1 and Der p 2 present in the highest concentration (w/v), more preferred above 85% of the concentration of the allergen selected from Der f 1, Der f 2, Der p 1 and Der p 2 present in the highest concentration (w/v), more preferred above 90% of the concentration of the allergen selected from Der f 1, Der f 2, Der p 1 and Der p 2 present in the highest concentration (w/v), more preferred above 95% of the concentration of the allergen selected from Der f 1, Der f 2, Der p 1 and Der p 2 present in the highest concentration (w/v), preferred above 98° A) of the concentration of the allergen selected from Der f 1, Der f 2, Der p 1 and Der p 2 present in the highest concentration (w/v), or most preferred above 99% of the concentration of the allergen selected from Der f 1, Der f 2, Der p 1 and Der p 2 present in the highest concentration (w/v).

Embodiment 5

The pharmaceutical product according to any one of embodiments 1-4 comprising an extract of Der p mite bodies and an extract of Der p faecal particles.

Embodiment 6

The pharmaceutical product according to any one of embodiments 1-4 comprising an extract of Der f mite bodies and an extract of Der f faecal particles.

Embodiment 7

The pharmaceutical product according to any one of embodiments 1-4 comprising an extract of Der p mite bodies and an extract of Der f mite bodies.

Embodiment 8

The pharmaceutical product according any one of embodiments 1-7 comprising an extract of Der p mite bodies, an extract of Der p faecal particles, an extract of Der f mite bodies and an extract of Der f 2 faecal particles.

Embodiment 9

The pharmaceutical product according to any one of embodiments 4-8, wherein the extract of Der p mite bodies is prepared from one fraction or combined fraction(s) of mite cultures said fraction(s) comprising more than 70% v/v Der p mite bodies, more preferred more than 75% v/v Der p mite bodies, more preferred more than 80% v/v Der p mite bodies, preferably more than 85% v/v Der p mite bodies, preferably more than 90% v/v Der p mite bodies, preferred more than 95% v/v Der p mite bodies and most preferred more than 98% v/v Der p mite bodies, and/or the extract of Der f mite bodies is prepared from one fraction or combined fraction(s) of mite cultures said fractions comprising more than 70% v/v Der f mite bodies, preferably more than 75% v/v Der f mite bodies, preferably more than 80% v/v Der f mite bodies, preferably more than 85% v/v Der f mite bodies, preferably more than 90% v/v Der f mite bodies, more preferred more than 95% v/v Der f mite bodies, and preferably more than 98% v/v Der f mite bodies.

Embodiment 10

The pharmaceutical product according to any one of embodiments 1-9, wherein the extract of Der p mite bodies is prepared from one Der p mite body fraction or combined Der p mite body fractions and where extraction of said fraction(s) of mite bodies results in an extract comprising by weight equal amounts of group 1 and group 2 allergen or more group 2 allergen than group 1 allergen and/or the extract of Der f mite bodies is prepared from one Der f mite body fraction or more combined Der f mite body fractions and where extraction of said fraction(s) of mite bodies results in an extract comprising by weight equal amounts by weight of group 1 and group 2 allergen or more group 2 allergen than group 1 allergen.

Embodiment 11

The pharmaceutical product according to any one of embodiments 1-10, wherein the extract of Der p mite bodies is prepared from one fraction or combined fraction(s) of mite cultures said fraction(s) comprising more than 70% v/v Der p mite bodies, more preferred more than 75% v/v Der p mite bodies, more preferred more than 80% v/v Der p mite bodies, preferably more than 85% v/v Der p mite bodies, preferably more than 90% v/v Der p mite bodies, preferred more than 95% v/v Der p mite bodies and most preferred more than 98% v/v Der p mite bodies, and/or the extract of Der f mite bodies is prepared from one fraction or combined fraction(s) of mite cultures said fractions comprising more than 70% v/v Der f mite bodies, preferably more than 75% v/v Der f mite bodies, preferably more than 80% v/v Der f mite bodies, preferably more than 85% v/v Der f mite bodies, preferably more than 90% v/v Der f mite bodies, more preferred more than 95% v/v Der f mite bodies, and preferably more than 98% v/v Der f mite bodies.

Embodiment 12

The pharmaceutical product according to any one of embodiments 1-11, wherein the extract of Der p faecal particles is prepared from one fraction or combined fraction(s) of mite cultures said fraction(s) comprising more than 70% v/v Der p faecal particles, preferably more than 75% v/v Der p faecal particles, preferably more than 80% v/v Der p faecal particles, preferably more than 85% v/v Der p faecal particles, preferably more than 90% v/v Der p faecal particles, more preferred more than 95% v/v Der p faecal particles, most preferred more than 98% v/v Der p faecal particles and/or the extract of Der f faecal particles is prepared from one fraction or combined fraction(s) of mite cultures said fraction(s) comprising more than 70% v/v Der f faecal particles, preferred more than 75% v/v Der f faecal particles, preferred more than 80% v/v Der f faecal particles, preferably more than 85% v/v Der f faecal particles, preferably more than 90% v/v Der f faecal particles, preferred more than 95% v/v, more preferred more than 98% v/v Der f faecal particles.

Embodiment 13

The pharmaceutical product according to embodiment 12, wherein a fraction or the combined fractions of mite bodies and/or wherein a fraction or the combined fractions of mite faecal particles each comprises below 10% v/v of mite culture medium.

Embodiment 14

The pharmaceutical product according to embodiment 13, wherein the mite body fraction or combined body fractions comprises up to 20% v/v mite parts (e.g. legs), faecal particles and mite medium.

Embodiment 15

The pharmaceutical product according to any one of embodiments 12-14, wherein the mite faecal fraction or combined faecal fractions comprises up to 20% v/v mite parts (e.g. legs) and mite medium.

Embodiment 16

The pharmaceutical product according to any one of embodiments 1-15, wherein the amount by weight of group 1 allergen is lower than the amount by weight of group 2 allergen in the extracts of mite body and the amount by weight of group 1 allergen is higher than the amount by weight of group 2 allergen in the extracts of mite faecal particles.

Embodiment 17

The pharmaceutical product according to any one of embodiments 1-16 comprising allergen extract, which comprises allergens selected from Der f 1, Der f 2, Der p 1 and Der p 2 and where the allergen present in the lowest concentration (w/v) in the allergen extract, is present in a concentration which is above 50% of the concentration of the allergen selected from Der f 1, Der f 2, Der p 1 and Der p 2 present in the highest concentration (w/v), more preferred above 60% of the concentration of the allergen selected from Der f 1, Der f 2, Der p 1 and Der p 2 present in the highest concentration (w/v), more preferred above 70% of the concentration of the allergen selected from Der f 1, Der f 2, Der p 1 and Der p 2 present in the highest concentration (w/v), more preferred above 80% of the concentration of the allergen selected from Der f 1, Der f 2, Der p 1 and Der p 2 present in the highest concentration (w/v), more preferred above 85% of the concentration of the allergen selected from Der f 1, Der f 2, Der p 1 and Der p 2 present in the highest concentration (w/v), more preferred above 90% of the concentration of the allergen selected from Der f 1, Der f 2, Der p 1 and Der p 2 present in the highest concentration (w/v), more preferred above 95% of the concentration of the allergen selected from Der f 1, Der f 2, Der p 1 and Der p 2 present in the highest concentration (w/v), preferred above 98% of the concentration of the allergen selected from Der f 1, Der f 2, Der p 1 and Der p 2 present in the highest concentration (w/v), or most preferred above 99% of the concentration of the allergen selected from Der f 1, Der f 2, Der p 1 and Der p 2 present in the highest concentration (w/v).

Embodiment 18

The pharmaceutical product according to any one of embodiments 1-17, wherein the pharmaceutical product is a compressed or non-compressed sublingual tablet(s) comprising the extract(s) or allergoids prepared from an extract(s), a liquid sublingual product comprising the extract(s) or allergoids prepared from extract(s), or a liquid product for injection comprising the extract(s) or allergoids prepared from extract(s).

Embodiment 19

The pharmaceutical product according to embodiment 18, wherein the pharmaceutical product is a fast dissolving sublingual tablet which comprises an extract.

Embodiment 20

The pharmaceutical product according to any of the embodiments 1-19, further comprising an extract of a whole mite culture or a body fraction(s) having less than 70% v/v of mite bodies.

Embodiment 21

The pharmaceutical product according to any of the embodiments 1-20 for the treatment and/or prevention of allergy and allergic asthma caused by house dust mites and/or for the diagnosis of allergy.

Embodiment 22

Use of the pharmaceutical product according to any of the embodiments 1-21, for the preparation of a medical product for the treatment and/or prevention of allergy and allergic asthma caused by house dust mites and/or for the diagnosis of allergy.

Embodiment 23

A mite body fraction comprising more than 70% v/v mite bodies, more preferred more than 75% v/v mite bodies, more preferred more than 80% v/v mite bodies, preferably more than 85% v/v mite bodies, preferably more than 90% v/v mite bodies, preferred more than 95% v/v mite bodies and most preferred more than 98% v/v mite bodies.

Embodiment 24

The mite body fraction according to embodiment 23, wherein the mite bodies are Der p mite bodies or Der f mite bodies.

Embodiment 25

The mite body fraction according to any one of embodiments 23-24 containing below 10% v/v culture media particles.

Embodiment 26

The mite body fraction according to any one of embodiments 23-25 comprising less than 20% v/v mite parts, faecal particles and mite medium.

Embodiment 27

An extract of a mite body fraction as defined in any one of embodiments 23-26 for use in a pharmaceutical product for the treatment and/or prevention of allergy and allergic asthma caused by house dust mites.

Embodiment 28

A mite faecal particle fraction comprising more than 70% v/v faecal particles, preferably more than 75% v/v faecal particles, preferably more than 80% v/v faecal particles, preferably more than 85% v/v faecal particles, preferably more than 90% v/v faecal particles, more preferred more than 95% v/v faecal particles, most preferred more than 98% v/v faecal particles.

Embodiment 29

The mite faecal particle fraction according to embodiment 28, wherein the faecal particles is Der p faecal particles or Der f faecal particles.

Embodiment 30

The mite faecal particle fraction according to any one of embodiments 28-29 comprising up to 20% v/v mite parts (e.g. legs) and mite medium.

Embodiment 31

An extract of a mite faecal particle fraction as defined in any one of embodiments 28-30 for use in a pharmaceutical product for the treatment and/or prevention of allergy and allergic asthma caused by house dust mites.

Embodiment 32

Use of an extract according to any one of embodiments 27 and 31 for the preparation of a pharmaceutical product for use in a pharmaceutical product for the treatment and/or prevention of allergy and allergic asthma caused by house dust mites.

Embodiment 33

A method for the manufacture of a mite allergen extract comprising Der p 1 and Der p 2 allergen, which method comprises the following steps:
  a. Isolating fraction(s) of Der p mite bodies from cultures of Der p mites, where said fraction(s) comprises more than 70% v/v Der p mite bodies, more preferred more than 75% v/v Der p mite bodies, more preferred more than 80% v/v Der p mite bodies, preferably more than 85% v/v Der p mite bodies, preferably more than 90% v/v Der p mite bodies, preferred more than 95% v/v Der p mite bodies and most preferred more than 98% v/v Der p mite bodies;
b. Optionally combining several of said fraction(s) of Der p mite bodies; and
c. Extracting allergens from said Der p mite body fraction(s) obtained in a step a) or a step b) as above to obtain said mite allergen extract.

Embodiment 34

A method for the manufacture of a mite allergen extract comprising Der f 1 and Der f 2 allergens, which method comprises the following steps:
a. Isolating fraction(s) of Der f mite bodies from cultures of Der f mites, where said fraction(s) comprises more than 70% v/v Der f mite bodies, more preferred more than 75% v/v Der f mite bodies, more preferred more than 80% v/v Der f mite bodies, preferably more than 85% v/v Der f mite bodies, preferably more than 90% v/v Der f mite bodies, preferred more than 95% v/v Der f mite bodies and most preferred more than 98% v/v Der f mite bodies;
b. Optionally combining several of said fraction(s) of Der f mite bodies; and
c. Extracting allergens from said Der f mite body fraction(s) obtained in a step a) or a step b) as above to obtain said mite allergen extract.

Embodiment 35

The method according any one of embodiments 33-34, which method further comprises the following step: mixing one or more mite allergen extract(s) of embodiment 33 with one or more mite allergen extract(s) of embodiment 34 to obtain a mixture of mite allergen extracts comprising Der p 1, Der p 2, Der f 1, and Der f 2 allergen.

Embodiment 36

The method according any one of embodiments 33-35, which method further comprises the following steps:
a. Isolating fraction(s) of Der p mite faecal particles from cultures of Der p mites;
b. Optionally combining several of said fraction(s) of Der p mite faecal particles;
c. Extracting allergens from Der p mite faecal particle fraction(s) obtained in a step a) or a step b) as above; and
d. Mixing one or more mite allergen extract(s) of any one of embodiments 33-35 with one or more extract(s) of faecal particles as obtained in a step c) above to obtain a mixture of mite allergen extracts.

Embodiment 37

The method according to any one of embodiments 33-36, which method further comprises the following steps:
a. Isolating fraction(s) of Der f mite faecal particles from cultures of Der f mites;
b. Optionally combining several of said fraction(s) of Der f mite faecal particles;
c. Extracting allergens from Der f mite faecal particle fraction(s) obtained in a step a) or a step b) as above; and
d. Mixing one or more mite allergen extract(s) of any one of embodiments 33-35 with one or more extract(s) of faecal particles as obtained in a step c) above to obtain a mixture of mite allergen extracts.

Embodiment 38

The method according to any one of embodiments 33-37, which method further comprises the following step: mixing one or more mite allergen extract(s) of embodiment 33 and embodiment 34 with one or more mite allergen extract(s) of step c in embodiment 36 and of step c in embodiment 37 to obtain a mixture of mite allergen extracts comprising Der p 1, Der p 2, Der f 1, and Der f 2 allergens.

Embodiment 39

The method according to any one of embodiments 33-38, wherein the obtained mite allergen extract is converted to an allergoid thereof.

Embodiment 40

The method according to any one of embodiments 33-39, which method comprises a further step of
a. Measuring the concentration (w/v) of group 1 and group 2 allergen in mite allergen extracts of step c) of any one of embodiments 33-34 and 36-37.

Embodiment 41

The method according to embodiment 40, which method comprises a further step of
e) Mixing one or more extract(s) of mite bodies of a step c) of any one of embodiments 33-34 with one or more extract(s) of faecal particles of a step c) of any one of embodiments 36-37 to obtain a mixture of mite allergen extracts with a predetermined amount by weight of group 1 to group 2 allergen.

Embodiment 42

The method according to any one of embodiments 33-41, wherein the mixture of mite allergen extract comprises extract(s) of Der p mite bodies, extract(s) of Der p faecal particles, extract(s) of Der f mite bodies and extract(s) of Der f 2 faecal particles.

Embodiment 43

The method according to any one of embodiments 33-42, wherein more than one fractions of mite bodies are combined according to step b) followed by extraction according to step c) of embodiment 33 and/or 34.

Embodiment 44

The method according to any one of embodiments 33-43, wherein more than one fraction of faecal particles are combined according to step b) followed by extraction according to step c) of embodiment 36 and/or 37.

Embodiment 45

The method according to any one of embodiments 33-44, wherein one or more extract(s) of mite bodies obtained in a step c) of embodiment 33 and/or 34 is mixed in a step e) with one or more extract(s) of mite faecal particles obtained in a step c) of embodiment 36 and/or 37.

Embodiment 46

The method according to any one of embodiments 33-45, wherein one or more extract(s) of mite bodies obtained in a step c) of embodiment 33 and/or 34 is mixed in a step e) with one extract of mite faecal particles obtained in a step c) of embodiment 36 and/or 37.

Embodiment 47

The method according to any one of embodiments 33-46, wherein one extract of mite bodies obtained in a step c) of embodiment 33 and/or 34 is mixed in a step with one or more extract(s) of mite faecal particles obtained in a step c) of embodiment 36 and/or 37.

Embodiment 48

The method according to any one embodiments 33-47, wherein a mite body extract(s) is supplemented with an amount by weight of faecal particles extract, a body extract from a body fraction of less than 70% v/v or a whole culture extract, which is sufficient to achieve a desired group 1 allergen to group 2 weight ratio in the mixture of mite allergen extracts.

Embodiment 49

The method according to any one of embodiments 33-48, wherein the extract of Der p faecal particles in step c) of embodiment 36 is prepared from one fraction or combined fraction(s) of mite cultures said fraction(s) comprising more than 70% v/v Der p faecal particles, preferably more than 75% v/v Der p faecal particles, preferably more than 80% v/v Der p faecal particles, preferably more than 85% v/v Der p faecal particles, preferably more than 90% v/v Der p faecal particles, more preferred more than 95% v/v Der p faecal particles, most preferred more than 98% v/v Der p faecal particles and/or the extract of Der f faecal particles in step c) of embodiment 37 is prepared from one fraction or combined fraction(s) of mite cultures said fraction(s) comprising more than 70% v/v Der f faecal particles, preferred more than 75% v/v Der f faecal particles, preferred more than 80% v/v Der f faecal particles, preferably more than 85% v/v Der f faecal particles, preferably more than 90% v/v Der f faecal particles, preferred more than 95% v/v, more preferred more than 98% v/v Der f faecal particles.

Embodiment 50

The method according to any one of embodiments 33-49, wherein a fraction of mite bodies in step a) or the combined fractions of mite bodies in step b) of embodiment 33 and/or 34 and/or wherein a fraction of faecal particles in step a) or the combined fractions of mite faecal particles in step b) of embodiment 36 and/or 37 each comprises below 10% v/v of mite culture medium.

Embodiment 51

The method according to embodiment 50, wherein the mite body fraction in step a) or the combined body fractions in step b) of embodiment 33 and/or 34 comprises up to 20% v/v mite parts (e.g. legs), faecal particles and mite medium.

Embodiment 52

The method according to embodiment 50, wherein the mite faecal fraction in step a) or combined faecal fractions in step b) of embodiment 36 and/or 37 comprises up to 20% v/v mite parts (e.g. legs) and mite medium.

Embodiment 53

The method according to any one of embodiments 33-52, wherein the fraction(s) of mite bodies of embodiment 33 and/or 34 and the fraction(s) of mite faecal particles in step a) of embodiment 36 and/or 37 is isolated from mite culture(s) by sieving of the Der p and/or Der f mite culture(s) to produce a mite body fraction b) and a mite faecal particles fraction d).

Embodiment 54

The method according to embodiment 33-53, wherein the fraction(s) of mite bodies and the fraction(s) of mite faecal particles is obtained by sieving of the Der p and/or Der f mite culture(s) to produce four fractions:
 a. Large medium particles>350 μm
 b. Mite body fraction 350-90 μm
 c. Faecal agglomerates and mite parts 90-50 μm
 d. Faecal particles<50 μm
 e. fraction a) and c) are discarded, fraction d) and b) are optionally subjected to further purification or used directedly for extraction.

Embodiment 55

The method according to embodiment 54, wherein mite body fraction b) is:
 ii) Subjected to density centrifugation in a first liquid medium having a higher density than the mite bodies and a lower density than the culture media particles; followed by
 iii) Collection of the mite bodies from said first liquid medium and optionally repeating step ii) and iii) until the desired purity of the mite bodies have been achieved, optionally followed by
 iv) Washing of the mite bodies to remove said first liquid with a second liquid.

Embodiment 56

A method for the isolation and purification of mite bodies comprising the steps:
 i) Isolating mite body fraction(s) from Der p or Der f mite culture(s) and
 ii) Subjecting one or more Der p mite body fraction(s), or one or more Der f mite body fraction(s), to density centrifugation in a first liquid medium having a higher density than the mite bodies and a lower density than the culture media particles; and
 iii) Collecting the mite bodies from said first liquid medium and optionally repeating step ii) and iii) until the desired purity of the mite bodies have been achieved, optionally followed by
 iv) Washing of the mite bodies to remove said first liquid with a second liquid.

Embodiment 57

A method for the isolation and purification of mite bodies comprising the steps:
 i) Isolating mite body fraction(s) from Der p or Der f mite culture(s) and ii) Subjecting one or more Der p mite body fraction(s), or one or more Der f mite body fraction(s), to density centrifugation in a first liquid medium having a higher density than the mite bodies and a lower density than the culture media particles; and
iii) Collecting the mite bodies from said first liquid medium, optionally followed by
iv) Washing of the mite bodies to remove said first liquid with a second liquid.

Embodiment 58

The method according to any one of embodiments 56-57, wherein the first and second liquids are anhydrous, preferably pharmaceutically acceptable liquids.

Embodiment 59

The method according to any one of embodiments 56-58, wherein the first liquid is anhydrous glycerol.

Embodiment 60

The method according to any one of embodiments 56-59, wherein the second liquid is anhydrous ethanol.

Embodiment 61

The method according to any one of embodiments 56-60, wherein step ii) and iii) is repeated once.

Embodiment 62

The method according to any one of embodiments 56-61, wherein step ii) and iii) are repeated until the mite body fraction obtained comprises at least 70% v/v mite bodies, more preferred more than 75% v/v mite bodies, more preferred more than 80% v/v mite bodies, preferably more than 85% v/v mite bodies, preferably more than 90% v/v mite bodies, preferred more than 95% v/v mite bodies and most preferred more than 98% v/v mite bodies.

Embodiment 63

The method of embodiment 56-62, wherein purification of the mite body fraction is continued until the mite body fraction contain below 10% v/v culture media particles.

Embodiment 64

The method of embodiment 63, wherein the purification of the mite body is continued until less than 20% v/v mite parts, faecal particles and mite medium is present.

Embodiment 65

The method of any one of embodiments 33-64, wherein fractions of Der f mite bodies, fractions of Der p mite bodies, fraction(s) of Der p faecal particles and/or fractions of Der f faecal particles in step a) of any one of embodiment 33-34 and 36-37 is isolated by a sieving process comprising:
1) Sieving Der f or Der p mite cultures in a vibrating sieve shaker with a tower of a 300, a 150 and a 80 μm mesh sieve followed by isolation of a mite body rich fraction between 150 μm and 300 μm and a mite faecal particles rich fraction below 80 μm, followed by
2) Sieving the mite body rich fraction (150 μm and 300 μm) in a sieve shaker with a horizontally and circular movement and with a tower of 200, 300 and/or 400 μm mesh sieves and isolating body fraction(s) captured by the 200, 300 and/or 400 μm mesh sieves, followed by
3) Sieving of the body rich fraction in a sieve shaker having a 3D throwing motion and 300, 200, 150 and 100 mesh sieve to produce a mite body fraction between 150 and 300 μm mesh and a mite faecal particles extract below 100 μm; and
4) Optionally combining the facal particles fraction below 80 μm from the vibrating sieve and the faecal particles fraction below 100 μm from the sieve with the 3D throwing motion and subjecting the combined faecal fraction to sieving in the sieve with the 3D throwing motion and a tower of 100, 80, 50 μm mesh sieves and isolating the faecal particles rich fraction blow 50 μm.

Embodiment 66

The method according to any one of embodiments 33-65, wherein the extracts or mixture of extracts obtained are formulated in a pharmaceutical product such as a compressed or non-compressed sublingual tablet(s) comprising the extract(s) or allergoids prepared from an extract(s), a liquid sublingual product comprising the extract(s) or allergoids prepared from extract(s), or a liquid product for injection comprising the extract(s) or allergoids prepared from extract(s).

Embodiment 67

The method according to embodiment 66, wherein the pharmaceutical product is a fast dissolving sublingual tablet which comprises an extract.

Embodiment 68

A pharmaceutical product prepared by a method as defined in any one of the embodiments 33-67.

Embodiment 69

The pharmaceutical product according to embodiment 68 for the treatment and/or prevention of allergy and allergic asthma caused by house dust mites.

Embodiment 70

An allergen extract of a series of allergen extracts for the use in a pharmaceutical allergen product for the treatment and/or prevention of allergy and allergic asthma caused by house dust mites, each allergen extract comprising at least one extract of mite bodies, and at least one extract of mite faecal particles, or a mite body extract from a fraction of mite bodies having less than 70% v/v mite bodies or an whole mite culture extract, wherein said allergen extract has a predetermined ratio of group 1 and group 2 allergen, and wherein the variance coefficient of said ratio is no more than 25, 20, 15, 10, or 7.5% for the series of extracts.

Embodiment 71

An allergen extract of an series of allergen extracts for the use in a pharmaceutical allergen product for the diagnosis of allergy caused by house dust mites, each allergen extract comprising at least one extract of mite bodies and at least one extract of mite faecal particles, or a mite body extract from a fraction of mite bodies having less than 70% v/v mite bodies or an whole mite culture extract, wherein said allergen extract has a predetermined ratio of group 1 and group 2 allergen, and wherein the variance coefficient of said ratio is no more than 25, 20, 15, 10, or 7.5% for the series of extracts.

Embodiment 72

The allergen extract according to any one of embodiments 70-71, wherein the amount by weight of group 1 allergen is lower than the amount by weight of group 2 allergen in the extracts of mite body and the amount by weight of group 1 allergen is higher than the amount by weight of group 2 allergen in the extracts of mite faecal particles.

Embodiment 73

The allergen extract according to any one of embodiments 70-72, wherein the allergen extract is as defined in any one of embodiments 1-32.

Embodiment 74

The allergen extract according to any one of embodiments 70-72, wherein the allergen extract is prepared as defined in any one of embodiments 33-66.

Further embodiments according to the invention:

Embodiment 1

A pharmaceutical product comprising an allergen extract (I) or an allergoid thereof for the treatment and/or prevention of allergy and allergic asthma caused by house dust mites comprising at least one extract of mite bodies and optionally at least one extract of mite faecal particles selected from the following groups a)-d):
a) An extract of Der p mite bodies,
b) An extract of Der p faecal particles,
c) An extract of Der f mite bodies, and
d) An extract of Der f faecal particles.

Embodiment 2

A pharmaceutical product comprising allergen extract (I) for the treatment and/or prevention of allergy and allergic asthma caused by house dust mites comprising allergens selected from Der f 1, Der f 2, Der p 1 and Der p 2 and where the allergen present in the lowest concentration (w/v) in the allergen extract (I), is present in a concentration which is above 50% of the concentration of the allergen selected from Der f 1, Der f 2, Der p 1 and Der p 2 present in the highest concentration (w/v), more preferred above 60% of the concentration of the allergen selected from Der f 1, Der f 2, Der p 1 and Der p 2 present in the highest concentration (w/v), more preferred above 70% of the concentration of the allergen selected from Der f 1, Der f 2, Der p 1 and Der p 2 present in the highest concentration (w/v), more preferred above 80% of the concentration of the allergen selected from Der f 1, Der f 2, Der p 1 and Der p 2 present in the highest concentration (w/v), more preferred above 85% of the concentration of the allergen selected from Der f 1, Der f 2, Der p 1 and Der p 2 present in the highest concentration (w/v), more preferred above 90% of the concentration of the allergen selected from Der f 1, Der f 2, Der p 1 and Der p 2 present in the highest concentration (w/v), more preferred above 95% of the concentration of the allergen selected from Der f 1, Der f 2, Der p 1 and Der p 2 present in the highest concentration (w/v), preferred above 98% of the concentration of the allergen selected from Der f 1, Der f 2, Der p 1 and Der p 2 present in the highest concentration (w/v), or most preferred above 99% of the concentration of the allergen selected from Der f 1, Der f 2, Der p 1 and Der p 2 present in the highest concentration (w/v).

Embodiment 3

A pharmaceutical product according to any of embodiments 1-2 comprising at least one extract of mite bodies and at least one extract of mite faecal particles.

Embodiment 4

The pharmaceutical product according to embodiment 3 comprising an extract of Der p mite bodies, an extract of Der p faecal particles, an extract of Der f mite bodies and an extract of Der f 2 faecal particles.

Embodiment 5

A pharmaceutical product according to any of embodiments 1-2 comprising an extract of Der p mite bodies and an extract of Der p faecal particles and no extracts of Der f mite bodies and no extracts of Der f faecal particles.

Embodiment 6

A pharmaceutical product according to any of embodiments 1-2 comprising an extract of Der f mite bodies and an extract of Der f faecal particles and no extracts of Der p mite bodies and no extracts of Der p faecal particles.

Embodiment 7

A pharmaceutical product according to any of embodiments 1-2 comprising an extract of Der p mite bodies and an extract of Der f mite bodies and no extract of mite faecal particles.

Embodiment 8

A pharmaceutical product according to any of embodiments 1-2 comprising an extract of Der p mite bodies and no extract of Der f mite bodies and no extract of mite faecal particles.

Embodiment 9

A pharmaceutical product according to any of embodiment 1-2 comprising an extract of Der f mite bodies and no an extract of Der p mite bodies extract and no extract of mite faecal particles.

Embodiment 10

A pharmaceutical product according to any of embodiments 1-9 wherein
the extract of Der p mite bodies is prepared from one Der p mite body fraction or combined Der p mite body fractions and where extraction of said fraction(s) of mite bodies results in an extract comprising by weight equal amounts of group 1 and group 2 allergen or more group 2 allergen than group 1 allergen and/or the extract of Der f mite bodies is prepared from one Der f mite body fraction or more combined Der f mite body fractions and where extraction of said fraction(s) of mite bodies results in an extract comprising by weight equal amounts by weight of group 1 and group 2 allergen or more group 2 allergen than group 1 allergen.

Embodiment 11

A pharmaceutical product according to any of embodiments 1-10 wherein
the extract of Der p mite bodies is prepared from one fraction or combined fraction(s) of mite cultures said fraction(s) comprising more than 70% v/v Der p mite bodies, more preferred more than 75% v/v Der p mite bodies, more preferred more than 80% v/v Der p mite bodies, preferably more than 85% v/v Der p mite bodies, preferably more than 90% v/v Der p mite bodies, preferred more than 95% v/v Der p mite bodies and most preferred more than 98% v/v Der p mite bodies,
the extract of Der f mite bodies is prepared from one fraction or combined fraction(s) of mite cultures said fractions comprising more than 70% v/v Der f mite bodies, preferably more than 75% v/v Der f mite bodies, preferably more than 80% v/v Der f mite bodies, preferably more than 85% v/v Der f mite bodies, preferably more than 90% v/v Der f mite bodies, more preferred more than 95% v/v Der f mite bodies, and preferably more than 98% v/v Der f mite bodies,
the extract of Der p faecal particles is prepared from one fraction or combined fraction(s) of mite cultures said fraction(s) comprising more than 70% v/v Der p faecal particles, preferably more than 75% v/v Der p faecal particles, preferably more than 80% v/v Der p faecal particles, preferably more than 85% v/v Der p faecal particles, preferably more than 90% v/v Der p faecal particles, more preferred more than 95% v/v Der p faecal particles, most preferred more than 98% v/v Der p faecal particles and/or
the extract of Der f faecal particles is prepared from one fraction or combined fraction(s) of mite cultures said fraction(s) comprising more than 70% v/v Der f faecal particles, preferred more than 75% v/v Der f faecal particles, preferred more than 80% v/v Der f faecal particles, preferably more than 85% v/v Der f faecal particles, preferably more than 90% v/v Der f faecal particles, preferred more than 95% v/v, more preferred more than 98% v/v Der f faecal particles.

Embodiment 12

The pharmaceutical product according to embodiment 11 wherein a fraction or the combined fractions of mite bodies and/or wherein a fraction or the combined fractions of mite faecal particles each comprises below 10% v/v of mite culture medium.

Embodiment 13

The pharmaceutical product according to embodiment 12 wherein the mite body fraction or combined body fractions comprises up to 20% v/v mite parts (e.g. legs), faecal particles and mite medium.

Embodiment 14

The pharmaceutical product according to embodiment 12 wherein the mite faecal fraction or combined faecal fractions comprises up to 20% v/v mite parts (e.g. legs) and mite medium.

Embodiment 15

The pharmaceutical product according to any of embodiments 1-14 wherein the amount by weight of group 1 allergen is lower than the amount by weight of group 2 allergen in the extracts of mite body and the amount by weight of group 1 allergen is higher than the amount by weight of group 2 allergen in the extracts of mite faecal particles.

Embodiment 16

The pharmaceutical product according to any of embodiments 1, 3-15 comprising allergen extract (I) for the treatment and/or prevention of allergy and allergic asthma caused by house dust mites comprising allergens selected from Der f 1, Der f 2, Der p 1 and Der p 2 and where the allergen present in the lowest concentration (w/v) in the allergen extract (I), is present in a concentration which is above 50% of the concentration of the allergen selected from Der f 1, Der f 2, Der p 1 and Der p 2 present in the highest concentration (w/v), more preferred above 60% of the concentration of the allergen selected from Der f 1, Der f 2, Der p 1 and Der p 2 present in the highest concentration (w/v), more preferred above 70% of the concentration of the allergen selected from Der f 1, Der f 2, Der p 1 and Der p 2 present in the highest concentration (w/v), more preferred above 80% of the concentration of the allergen selected from Der f 1, Der f 2, Der p 1 and Der p 2 present in the highest concentration (w/v), more preferred above 85% of the concentration of the allergen selected from Der f 1, Der f 2, Der p 1 and Der p 2 present in the highest concentration (w/v), more preferred above 90% of the concentration of the allergen selected from Der f 1, Der f 2, Der p 1 and Der p 2 present in the highest concentration (w/v), more preferred above 95% of the concentration of the allergen selected from Der f 1, Der f 2, Der p 1 and Der p 2 present in the highest concentration (w/v), preferred above 98% of the concentration of the allergen selected from Der f 1, Der f 2, Der p 1 and Der p 2 present in the highest concentration (w/v), or most preferred above 99% of the concentration of the allergen selected from Der f 1, Der f 2, Der p 1 and Der p 2 present in the highest concentration (w/v).

Embodiment 17

The pharmaceutical product according to any of embodiments 1-16, wherein the pharmaceutical product is a compressed or non-compressed sublingual tablet(s) comprising the extract (I) or allergoids prepared from an extract (I) in a solid form, a liquid sublingual product or a liquid product for injection comprising the extract (I) or allergoids prepared from extract (I), preferably the pharmaceutical product is a fast dissolving sublingual tablet which comprises an extract (I) in solid form.

Embodiment 18

A method for the manufacture of a mite allergen extract (I) or allergoids thereof for a pharmaceutical product according to any of embodiments 1-10 and 15-16 said allergen extract (I) having a predetermined and controlled amount by weight of allergens selected from Der f 1, Der f 2, Der p 1 and Der p 2 allergens and comprising the following steps:
a) Fractions of Der p mite bodies and/or fractions of Der p mite faecal particles are isolated from Der p cultures of mites, and/or fractions of Der f mite bodies and/or fractions of Der f mite faecal particles are isolated from Der f mite cultures;

b) Optionally combining several fractions of Der p mite bodies, optionally combining several fractions of Der p mite faecal particles, optionally combining several fractions of Der f mite bodies and optionally combining several fractions of Der f mite faecal particles;

c) Extracting allergens from mite body faction(s) obtained in a step a) or a step b) as above and/or extraction of allergens from mite faecal particle fraction(s) obtained in a step a) or a step b) as above; and thereafter d) Measuring the concentration (w/v) of group 1 and group 2 allergen in mite allergen extracts obtained in a step c) as above; and optionally e) Mixing one or more extract(s) of mite bodies with one or more extract(s) of faecal particles as obtained in a step c) as above to obtain a mixture of allergen extracts (I) with a predetermined amount by weight of group 1 to group 2 allergen and optionally f) Converting the extract (I) to an allergoid thereof.

Embodiment 19

The method according to embodiment 18 wherein one or more extract(s) of mite bodies and one or more extract(s) of faecal particles is mixed to obtain a mixture of allergen extracts (I).

Embodiment 20

The method according to embodiments 18-19 wherein the mixture of mite allergen extract (I) comprises extract(s) of Der p mite bodies, extract(s) of Der p faecal particles, extract(s) of Der f mite bodies and extract(s) of Der f 2 faecal particles.

Embodiment 21

The method according to any of embodiments 18-20 wherein more than one fractions of mite bodies are combined according to step b) followed by extraction according to step c).

Embodiment 22

The method according to any of embodiments 18-21 wherein more than one fraction of faecal particles are combined according to step b) followed by extraction according to step c).

Embodiment 23

The method according to any of embodiments 18-22 wherein one or more extract(s) of mite bodies obtained in a step c) is mixed in a step e) with one or more extract(s) of mite faecal particles obtained in a step c).

Embodiment 24

The method according to any of embodiments 18-23 wherein one or more extract(s) of mite bodies obtained in a step c) is mixed in a step e) with one extract of mite faecal particles obtained in a step c).

Embodiment 25

The method according to any of embodiments 18-24 wherein one extract of mite bodies obtained in a step c) is mixed in a step e) with one or more extract(s) of mite faecal particles obtained in a step c).

Embodiment 26

The method according to any of embodiment 18-25 wherein a mite body extract(s) is supplemented with an amount by weight of faecal particles extract which is sufficient to achieve the desired group 1 allergen to group 2 weight ratio in the mixture of mite allergen extracts (I).

Embodiment 27

A method according to any of embodiments 14-26 wherein
the extract in of Der p mite bodies in step c) is prepared from one fraction or combined fraction(s) of mite cultures said fraction(s) comprising more than 70% v/v Der p mite bodies, more preferred more than 75% v/v Der p mite bodies, more preferred more than 80% v/v Der p mite bodies, preferably more than 85% v/v Der p mite bodies, preferably more than 90% v/v Der p mite bodies, preferred more than 95% v/v Der p mite bodies and most preferred more than 98% v/v Der p mite bodies, the extract of Der f mite bodies in step c) is prepared from one fraction or combined fraction(s) of mite cultures said fractions comprising more than 70% v/v Der f mite bodies, preferably more than 75% v/v Der f mite bodies, preferably more than 80% v/v Der f mite bodies, preferably more than 85% v/v Der f mite bodies, preferably more than 90% v/v Der f mite bodies, more preferred more than 95% v/v Der f mite bodies, and preferably more than 98% v/v Der f mite bodies, the extract of Der p faecal particles in step c) is prepared from one fraction or combined fraction(s) of mite cultures said fraction(s) comprising more than 70% v/v Der p faecal particles, preferably more than 75% v/v Der p faecal particles, preferably more than 80% v/v Der p faecal particles, preferably more than 85% v/v Der p faecal particles, preferably more than 90% v/v Der p faecal particles, more preferred more than 95% v/v Der p faecal particles, most preferred more than 98% v/v Der p faecal particles and/or the extract of Der f faecal particles in step c) is prepared from one fraction or combined fraction(s) of mite cultures said fraction(s) comprising more than 70% v/v Der f faecal particles, preferred more than 75% v/v Der f faecal particles, preferred more than 80% v/v Der f faecal particles, preferably more than 85% v/v Der f faecal particles, preferably more than 90% v/v Der f faecal particles, preferred more than 95% v/v, more preferred more than 98% v/v Der f faecal particles.

Embodiment 28

The method according to embodiment 27 wherein a fraction of mite bodies in step a) or the combined fractions of mite bodies in step b) and/or wherein a fraction of faecal particles in step a) or the combined fractions of mite faecal particles in step b) each comprises below 10% v/v of mite culture medium.

Embodiment 29

The method according to embodiment 28 wherein the mite body fraction in step a) or the combined body fractions in step b) comprises up to 20% v/v mite parts (e.g. legs), faecal particles and mite medium.

Embodiment 30

The method according to embodiment 29 wherein the mite faecal fraction in step a) or combined faecal fractions in step b) comprises up to 20% v/v mite parts (e.g. legs) and mite medium.

Embodiment 31

The method according to any of embodiments 18-30 wherein the fraction(s) of mite bodies and the fraction(s) of mite faecal particles in step a) of embodiment 18 is isolated from mite culture(s) by sieving of the Der p and/or Der f mite culture(s) to produce a mite body fraction b) and a mite faecal particles fraction d).

Embodiment 32

The method according to embodiment 31 wherein the fraction(s) of mite bodies and the fraction(s) of mite faecal particles is obtained by sieving of the Der p and/or Der f mite culture(s) to produce four fractions:
a) Large medium particles>350 μm
b) Mite body fraction 350-90 μm
c) Faecal agglomerates and mite parts 90-50 μm prepared
d) Faecal particles<50 μm
fraction a) and c) are discarded, fraction d) is used directly for extraction and fraction b) is subjected to further purification.

Embodiment 33

A method for the isolation and purification of mite bodies comprising the steps:
i) Isolating mite body fraction(s) from Der p or Der f mite culture(s) and
ii) Subjecting one or more Der p mite body fraction(s), or one or more Der f mite body fraction(s), to density centrifugation in a first liquid medium having iia) a higher density than the mite bodies and a lower density than the culture media particles and iib) do not extract group 1 and group 2 allergen form the mite bodies; and
iii) Collecting the mite bodies from the surface of said first liquid medium and optionally repeating step ii) and iii) until the desired purity of the mite bodies have been achieved, optionally followed by
iv) Washing of the mite bodies to remove said first liquid with a second liquid that does not extract group 1 and group 2 allergen from the mite bodies.

Embodiment 34

The method according to any of embodiments 31-32 wherein mite body fraction b) is:
ii) Subjected to density centrifugation in a first liquid medium having iia) a higher density than the mite bodies and a lower density than the culture media particles and iib) do not extract group 1 and group 2 allergen form the mite bodies; followed by
iii) Collection of the mite bodies from the surface of said first liquid medium and optionally repeating step ii) and iii) until the desired purity of the mite bodies have been achieved, optionally followed by
iv) washing of the mite bodies to remove said first liquid with a second liquid that does not extract group 1 and group 2 allergen from the mite bodies.

Embodiment 35

The method according to any of embodiments 33 or 34 wherein the first and second liquids are anhydrous, preferably pharmaceutically acceptable liquids.

Embodiment 36

A method according to embodiment 35 wherein the first liquid is anhydrous glycerol.

Embodiment 37

A method according to embodiment 36 wherein the second liquid is anhydrous ethanol.

Embodiment 38

The method according to embodiment 33-37 wherein step ii) and iii) is repeated once.

Embodiment 39

The method of any of embodiments 33-37 wherein step ii) and iii) are repeated until the mite body fraction obtained comprises at least 70% v/v mite bodies, more preferred more than 75% v/v mite bodies, more preferred more than 80% v/v mite bodies, preferably more than 85% v/v mite bodies, preferably more than 90% v/v mite bodies, preferred more than 95% v/v mite bodies and most preferred more than 98% v/v mite bodies.

Embodiment 40

The method of embodiment 31-33 and 38-39 wherein purification of the mite body fraction is continued until the mite body fraction contain below 10% v/v culture media particles.

Embodiment 41

The method of embodiment 40 wherein the purification of the mite body is continued until less than 20% v/v mite parts, faecal particles and mite medium is present.

Embodiment 42

A mite body fraction comprising more than 70% v/v mite bodies, more preferred more than 75% v/v mite bodies, more preferred more than 80% v/v mite bodies, preferably more than 85% v/v mite bodies, preferably more than 90% v/v mite bodies, preferred more than 95% v/v mite bodies and most preferred more than 98% v/v mite bodies.

Embodiment 43

A mite body fraction according to embodiment 42 containing below 10% v/v culture media particles.

Embodiment 44

A mite body fraction according to embodiment 43 comprising less than 20% v/v mite parts, faecal particles and mite medium.

Embodiment 45

The method of any of embodiments 18-30 wherein fractions of Der f mite bodies, fractions of Der p mite bodies, fraction(s) of Der p faecal particles and/or fractions of Der f faecal particles in step 18 a) is isolated by a sieving process comprising:

1) Sieving Der f or Der p mite cultures in a vibrating sieve shaker with a tower of a 300, a 150 and a 80 μm mesh sieve followed by isolation of a mite body rich fraction between 150 μm and 300 μm and a mite faecal particles rich fraction below 80 μm, followed by 2) Sieving the mite body rich fraction (150 μm and 300 μm) in a sieve shaker with a horizontally and circular movement and with a tower of 200, 300 and/or 400 μm mesh sieves and isolating body fraction(s) captured by the 200, 300 and/or 400 μm mesh sieves, followed by 3) Sieving of the body rich fraction in a sieve shaker having a 3D throwing motion and 300, 200, 150 and 100 mesh sieve to produce a mite body fraction between 150 and 300 μm mesh and a mite faecal particles extract below 100 μm; and 4) Optionally combining the facal particles fraction below 80 μm from the vibrating sieve and the faecal particles fraction below 100 μm from the sieve with the 3D throwing motion and subjecting the combined faecal fraction to sieving in the sieve with the 3D throwing motion and a tower of 100, 80, 50 μm mesh sieves and isolating the faecal particles rich fraction blow 50 μm.

Embodiment 46

The method according to any of embodiments 18-41, 45 wherein the mixture of extracts (I) obtained is formulated as a compressed or non compressed sublingual tablet(s) comprising the extract (I) or allergoids prepared from extract (I) in a solid form, a liquid sublingual product or a liquid product for injection comprising the extract (I) or allergoids prepared from extract (I), preferably the pharmaceutical product is a fast dissolving sublingual tablet which comprises an extract (I) in solid form.

EXPERIMENTAL SECTION

Example 1

1.0 Cultivation of Mites

Der p and Der f mites are cultivated separately on a suitable medium with medium particles which are of sufficient size and integrity to withstand the rigors of downstream processing and be easily eliminated through the primary screening process. The mite medium suitably contains a protein source, carbohydrates, minerals, oil, vitamins and a preservative.

Mites are killed by freezing at −20° C.±5° C. when the optimal growth have been reach.

1.1 Purification of Mite Bodies and Mite Faecal Particles

The mite culture (Der p or Der f) is dried to moisture content below 15% and sieved to produce four fractions:

1) Large medium particles>350 μm
2) Mite body fraction 350-90 μm
3) Faecal agglomerates and mite parts 90-50 μm
4) Faecal particles<50 μm An automated sieving unit is used to screen the dried mite culture. The siever uses rotation at set angles and speed to obtain fractions. The screen that produces fractions 1, 2 and 3 above can be de-blinded during sieving. The fines (fraction 4) are collected in the bottom pan of the sieving unit.

The large medium particles in fraction 1 and the faecal agglomerates and mite parts in fraction 3 are discarded.

The quality of the faecal particles in fraction 4 is tested (to assure that the fraction contains mostly faecal particles and meets release specifications) and it is decided whether the fraction is suitable for extraction of Der p or Der f allergens.

The v/v % of whole mite bodies, mite body parts, faecal particles, mite media and contaminants are measured by microscopy of samples, see page 13-14.

Several mite faecal fractions may be combined before extraction.

1.2.1 Purification of Mite Bodies Fraction 2 by Centrifugation with Glycerol

Centrifugation of fraction 2 is carried out in a (Beckman J6MI centrifuge).

Not more than 900 grams of fraction 2 is slowly added to USP anhydrous glycerine (99.0-101.0% pure) in an amount that is five times the weight of fraction 2.

The mite culture mixed with anhydrous glycerine is poured into centrifugation cups so that all cups contain the same volume. The cups are placed in the rotor and the cubs are centrifuged at 3000 rpm for 7 minutes at −5° C. The mite body plug formed is removed from the surface of the anhydrous glycerine and weighed. The mite bodies are mixed with an amount of anhydrous glycerine 3 times the weight of the mite body fraction and centrifugation is repeated.

The mite body plug is carefully removed from the surface of the anhydrous glycerine and weighed. The weight of the mite bodies is multiplied by 2.5 to determine the minimum amount by weight of anhydrous ethanol needed to form a slurry. The mite body and ethanol slurry is mixed for 5 minutes in a mixing vessel equipped with a low-shear blade. The slurry is poured onto two 106 micron sieves with a collection a collection pan.

Scrape the mite bodies from the sieves and record the weight of the mites. Repeat the last purification step with ethanol one more time and dry the mite bodies using vacuum or are allowed to dry on the 106 sieve in a fume hood.

The v/v % of whole mite bodies, mite body parts, faecal particles, mite media and contaminants are measured by microscopy of samples, see page 13-14. The mite body fraction achieved typically comprises 98-99 vol/vol % whole mite bodies.

1.2.2

Mite bodies from four different lots are subjected to purification as generally outlined above in example 1.2.1

In short, a centrifugation slurry was formed from mite culture fraction and anhydrous glycerine either 4, 5 or 6 times (weight ratio) and poured into centrifugation cups (up to 6 cups at the per run) which were centrifuged once or twice at 2500 rpm or 3500 rpm, where after the mite body plug were removed and washed 3 time with ethanol. The v/v % of whole mite bodies, mite body parts, faecal particles, mite media and contaminants were measured by microscopy of samples see example 1.4.

The results show a yield increase when centrifugation once in each of the four *D. pteronyssinus* lots processed, with the increase ranging from 72-156% with the average being 102%. For mites of the species *D. farinae* the % increase ranged from 83-111% with the average being 93.5%.

The purity levels of the resulting body fractions obtained were all above 97%, with faecal particle contents of below 2% medium contents of 2% or below. The group 1 to group 2 ratio were below 1.

Mite body fractions from different mite cultures may be mixed.

1.3 Purification of Mite Bodies Fraction 2 by Centrifugation with Saturated NaCl Mite body fraction 2 are mixed with saturated NaCl (in an amount that is five times the weight of fraction 2) to a slurry. The slurry is centrifuged at 3.000 RPM in 7 min (15° C. in a Sorvall centrifuge). Mite body plug is carefully removed from the surface and resuspended in an amount NaCl that is five times the weight and the centrifugation is repeated. The v/v % of whole mite bodies, mite body parts, faecal particles, mite media and contaminants are measured by microscopy of samples, see page 13-14.

The mite body fraction achieved typically comprises 98-99 vol/vol % whole mite bodies.

Table 1b:
1 and 2 are saturated salt water 1 spin, #3 and 4 are saturated salt water 2 spin TABLE 1b

| | Volumetric Percent Composition | | |
|---|---|---|---|
| Sample ID | Bodies | Faecals | Medium |
| 1 | 98,200 | 1.180 | 0.620 |
| 2 | 98,100 | 1.230 | 0.660 |
| 3 | 99,890 | 0.110 | 0.000 |
| 4 | 99,860 | 0.140 | 0.000 |

Example 2

2.0 Purification of Mite Bodies and Mite Faecal Particles

Place frozen culture on trays inside the purification room. Make sure the culture is spread in an even layer on the trays and let the culture thaw and dry at ambient conditions for 4-14 days.

The culture is then fluidized to dry it and to separate it in 2 fractions, see FIG. 1. An air flow is applied connecting a vacuum pump in one side and an air inlet in the other.

The glass containers in FIG. 1 are named from left to right "A" with the whole mite culture, "B" is rich in body particles and "C" is faecal particles.

The two fractions (B) and (C) are isolated and subjected to sieving.

2.1 Purification of Mite Bodies
2.1.1 Big Sieve

Fractions B are added to a continuous charge industrial vibratory Filtra FT 500 sieve shaker. The sieve has a tower of three meshes: 300, 150, and 80 μm and work at 1500 rpm.

The material above 300 μm is mainly food particles and is discarded.

The material below 80 μm is further purified in small sieve to isolate faecal fraction.

The material below 300 μm and above 150 μm was isolated as a body rich fraction and sieved in the medium sieve below.

2.1.2 Medium Sieve

Mites have a form which is not regular and can reach 400 μm in one dimension but are usually smaller in dry form. Mites have legs and hairs and when a horizontal circular motion is used during sieving the mite bodies are oriented horizontally forcing the formation tangles. Only a few disorientated particles or smaller particles not forming part of the tangle enter the mesh and the sieve is not blocked so quickly.

The sieve used is a Retsch AS 400 sieve shaker with a tower of 400, 300 and 200 μm meshes. A horizontal circular sieving mode is used and the sieving process takes advantage of the formation of tangles of mites having a size above 200, 300 and/or 400 μm.

The material from big sieve is divided in 150-200 g portions and added to the second (medium sieve).

The sieve work at a speed between 210 to 240 rpm and each batch are sieved for 1-2 minutes.

Fractions above 200, and 300 μm are reprocessed 2-6 times.

The content of mite bodies captured on the 200, 300 and/or 400 μm mesh sieves is determined by microscopic inspection of the fractions and the body rich fraction is isolated an subjected to further sieving as described below.

2.1.3 Small Sieve

The body rich fraction recovered from the Medium sieve is then subjected to sieving in a small sieve (Retsch AS 200) using a 3-D throwing motion. The mean amount of body rich fraction loaded into the sieve is 60 g and A tower of 300, 200, 150 and 100 mesh is used.

The speed is set to 240-260 rpm, the amplitude is set to 30 seconds and each load is sieved for 5-15 minutes. Each load is reprocessed 1-6 times.

In process controls: During the sieving process purity of the fraction is tested using a microscope.

The fraction below 100 μm was isolated as a faecal particles fraction which was purified as described below.

The fractions above 100 μm and 150 μm are isolated as mite body fractions.

2.2 Purification of Faecal Fraction

The faecal rich fractions obtained in previous steps (fraction C of pre-treatment step, fraction<80 μm of big sieve-shaker and fraction<100 μm of small sieve-shaker) are combined.

The small sieve-shaker (Retsch AS 200) is used with a tower of 100, 80 and 50 μm mesh and the operation conditions were the same as mentioned above for this sieve.

The fraction below 50 μm is isolated as the faecal fraction.

In process controls: During the sieving process purity grade of the fractions is estimated using a microscope.

Example 3

3.0 Extraction Mite Bodies

Mite bodies were suspended using a high shear mixer (20 min). Extraction was carried out in a buffer containing 0.012 M $NaHCO_3$, 0.154 M NaCl, at a pH of 7.5 for 3 hours at a temperature of 8° C. The mite body to buffer were 1+10 (w/w).

3.0.1 Separation

The remaining insoluble source material is separated from the extract solution by centrifugation.

After centrifugation the resulting centrifugate is decanted from the solid fraction and clarified through a filter into a filtrate solution. After filtration of the allergen extract, the filter is washed with extraction buffer and pooled to increase yield.

3.0.2 Ultrafiltration

The ultrafiltration is performed in three steps: Concentration step, Diafiltration step and dry matter adjustment step. Firstly, the filtrate solution is concentrated by removing water and other small molecules by tangential flow filtration. Secondly, small molecules and salts are removed from the allergen extract solution by diafiltration against purified water. Thirdly, the dry matter (DM) concentration of the allergenic extract is adjusted by further concentration or addition of purified water. During ultrafiltration the temperature and trans-membrane pressure (TMP) are monitored and kept within the acceptance criteria.

In Process Control:
Temperature: 3-15° C.
Trans Membrane Pressure: ≤3 bar
DM concentration: 40-60 mg/ml 3.0.3 Clarification Filtration The allergen extract solution is clarified through a 0.2 μm filter.

3.04 Stabilization

After filtration the extract is dispensed as free-falling droplets into a container filled with liquid nitrogen where the droplets freeze immediately. The liquid nitrogen is then allowed to evaporate. During the stabilization process the feed flow (product flow) is controlled to be within the acceptance criteria.

In process control: Product flow: 8-12 ml/min/dispensing hole.

3.1 Faecal Particles

The mite faecal particles are suspended using a high shear mixer (20 min). Extraction was carried out in a buffer containing 0.012 M $NaHCO_3$, 0.154 M NaCl, at a pH of 7.5 for 1 hour at a temperature of 8° C. The mite body to buffer ratio is 1+10 (w/w).

3.1.1 Separation

After extraction the insoluble source material is separated from the allergen solution by a diafiltration step. The diafiltration is performed using a vibrating membrane filtration system (TFF technique). The allergen extract passes through the membrane as permeate, while the insoluble source material will be retained by the membrane. During the diafiltration process a pre-defined volume of purified water is added continuously to the recirculating extract solution at the same rate as the allergen extract (permeate) is collected from the other side of the membrane.

In Process Control:
Permeate flux: 18-22 liter/m2/hour
Temperature: 4-12° C.

3.1.2 Ultrafiltration

The ultrafiltration is performed in three steps: Concentration step, Diafiltration step and Dry matter adjustment step. Firstly, the filtrate solution is concentrated by removing water and other small molecule by tangential flow filtration. Secondly, small molecules and salts are removed from the allergen extract solution by diafiltration against purified water. Thirdly, the dry matter (DM) concentration of the allergenic solution is adjusted by further concentration or addition of purified water. During ultrafiltration the tempera-ture and trans membrane pressure (TMP) are monitored as in-process controls and kept within the acceptance criteria.

In Process Control:
Temperature: 3-15° C.
Trans membrane pressure: 3 bar
DM concentration: 40-60 mg/ml

3.1.3 Clarification Filtration

The allergenic solution is clarified through a 0.2 μm filter.

3.1.4 Stabilization

After filtration the allergenic extract is dispensed as free-falling droplets into a container filled with liquid nitrogen where the droplets freeze immediately. The liquid nitrogen is then allowed to evaporate. During the stabilization process the feed flow (product flow) is controlled to be within in acceptance criteria.

In Process Control:
Product flow: 8-12 ml/min/dispensing hole

Example 4

The content of group 1 and group 2 allergen is measured by MS (mass spectrometry as described in WO 2007/031080 using the following calibration standard peptides:

(Der p 1)
SEQ ID NO: 1
TNACSINGNAPAEIDLR, (Der f 1)
SEQ ID NO: 2
NSWDTTWGDSGYGYFQAGNNLMMIEQYPYVVIM, (Der p 2)
SEQ ID NO: 3
VLVPGCHGSEPCIIHR, (Der f 2)
SEQ ID NO: 4
GKPFTLEALFDANQNTK,
and (Der f 1)
SEQ ID NO: 5
GIEYIQQNGVVEER

Example 5

5.0 Mixing of Extracts

Frozen balls of mite body extract were added frozen balls of faecal particles extract to achieve the desired ratio of group 1 and group 2 allergen.

The determination of which batches of frozen balls to be used and the number of frozen balls to be used is an iterative process.

The mixture with the desired ratio is created by calculating the amount by weight of group 1 allergen that will result from mixing of a number of balls from at least one batch of mite body extracts and at least one batch of mite faecal particles. The amount by weight of group 1 allergen is calculated as the amount by weight of any batch multiplied with the concentration of group 1 allergen in said batch. The amount by weight of group 2 allergen resulting from mixing the same batches is calculated in the same way.

More batches or parts of batches are added or removed from the calculation as described on page 27 above until the desired ratio is achieved.

Example

TABLE 2

| Extract (IM) | Name ($m_{F1}$, $m_{B1}$, $m_{F2}$, $m_{B2}$, etc.) | Production batch No. | Major allergen group 1 [μg grp. 1/ml IM] | Major allergen group 2 [μg/ml IM] |
|---|---|---|---|---|
| Body | $m_{B1}$ | IMPTE2001-B | 991 | 1223 |
| Faecal | $m_{F1}$ | IMPTE2001-F | 2393 | 792 |

The amount of extracts from each batch is calculated to be 140 gram mf1 and 966 gram mb1

Major allergen ratio=1=Total group 1/Total group 2=$mf1 \times Cf1\text{grp}1+mb1 \times Cb1\text{grp}1/mf1 \times Cf1\text{grp}2+mb1 \times Cb1\text{grp}2$=2393·140+991·966/792·140+1223·966=1

The frozen balls required are thereafter thawed and mixed and optionally frozen as balls again. Thawed mixtures may be used in the formulation process.

Example 6

The group 1 and group 2 allergens are determined as described in example 5.

| Batch | FAR1 | FAR2 | FAR3 | FAR4 | FAR5 | FAR5 | FAR6 | FAR7 | CV (in %)* |
|---|---|---|---|---|---|---|---|---|---|
| Ratio (Der 1/Der 2) | 0.96 | 0.97 | 1.00 | 0.95 | 0.89 | 0.88 | 0.95 | 0.95 | 6 |
| Batch | PTE1 | PTE2 | PTE3 | PTE4 | PTE5 | PTE6 | PTE7 | PTE7 | CV (In %)* |
| Ratio (Der 1/Der 2) | 1.04 | 1.17 | 0.94 | 1.01 | 1.00 | 1.03 | 1.10 | 1.01 | 6.5 |

*CV = relative standard deviation (SD/mean), with 95% CI

Example 7

6.1 Preparation of a Fast Dissolving Pharmaceutical Composition Containing an Extract Composition of house dust mite tablet before sublimation of water during freeze-drying:

TABLE 3

| Name of Ingredient | Weight Ratio of group 1 to group 2 allergen | Function |
|---|---|---|
| Active Ingredient | | |
| Der p mite body extract | 1:1:1:1 | Active Ingredient |
| Der p faecal particles extract | | |
| Der f mite body extract | | |
| Der f faecal particles extract | | |
| Other Ingredients | | |
| Gelatin (Fish) | 15 mg | Former of freeze-dried tablet structure |
| Mannitol | 12.7 mg | Former of freeze-dried tablet structure |

TABLE 3-continued

| Name of Ingredient | Weight Ratio of group 1 to group 2 allergen | Function |
|---|---|---|
| Sodium Hydroxide to pH 7.5 | qs | pH adjustment |
| Purified Water | qs to 250 mg | Vehicle |
| Total Wet Dosing Weight | 250 mg | — |

Preparation of the Tablet:

Gelatin, mannitol and purified water are mixed and the resulting premix is heated to appropriate temperature. Following cooling, the pH of the solution is adjusted using sodium hydroxide solution (~6% w/w). The drug substances are added to the premix as frozen droplets. The pH of the mix is tested and adjusted, if necessary. Additional amounts of purified water required to complete the formulation is calculated using the manufacturing formula and transferred to the mix solution. The solution is dosed into pre-formed blister trays. After dosing, the filled blister packs are passed through a liquid nitrogen freeze tunnel. All frozen products are immediately placed in a refrigerated cabinet for frozen storage prior to freeze-drying. The units are freeze-dried and stored in a dry storage cabinet in a controlled humidity environment until sealing. The freeze-dried units are then sealed with foil.

All patents, patent applications and non-patent literature cited herein are hereby incorporated by reference.

The invention claimed is:

1. A method of manufacturing multiple batches of a pharmaceutical composition, wherein each batch of said pharmaceutical composition comprises at least two active ingredients selected from the group consisting of Der p 1, Der f 1, Der p 2 and Der f 2, and
wherein the ratio of active ingredients selected from the group consisting of Der p 1, Der f 1, Der p 2 and Der f 2, respectively, has a batch-to-batch consistency coefficient of variation of less than 25%;
said method comprising:
  (a) separating at least two dust mite fractions from a dust mite culture, said separating step comprising:
    1) separating from at least one culture of Der f mites comprising Der f 1 and Der f 2 allergens, (i) a fraction of Der f mite bodies, comprising greater than 70% v/v Der f mite bodies and (ii) a fraction of Der f faecal particles; or
    2) separating from at least one culture of Der p mites comprising Der p 1 and Der p 2 allergens, (i) a fraction of Der p mite bodies, comprising greater than 70% v/v Der p mite bodies and (ii) a fraction of Der p faecal particles; or
    3) (A) separating from at least one culture of Der p mites comprising Der p 1 and Der p 2 allergens, (i) a fraction of Der p mite bodies, comprising greater than 70% v/v Der p mite bodies and (ii) a fraction of Der p faecal particles, and
    (B) separating from at least one culture of Der f mites comprising Der f 1 and Der f 2 allergens, (i) a fraction of Der f mite bodies, comprising greater than 70% v/v Der f mite bodies and (ii) a fraction of Der f faecal particles;
  (b) extracting, from each of said fractions from step (a), group 1, group 2, or groups 1 and 2 mite allergens to obtain mite allergen extracts comprising at least two active ingredients selected from the group consisting of Der p 1, Der f 1, Der p 2 and Der f 2;
  (c) measuring at least the amount of group 1, group 2 or group 1 and group 2 mite allergens in each extract from step (b);
  (d) combining amounts of said extracts from step (b) to yield an active ingredient mixture having a first ratio of active ingredients;
  (e) formulating said active ingredient mixture from step (d) into a first batch of said pharmaceutical composition comprising at least two active ingredients selected from the group consisting of Der p 1, Der f 1, Der p 2 and Der f 2;
  (f) repeating steps (a) through (e) to formulate a subsequent batch of said pharmaceutical composition wherein the ratio of active ingredients selected from the group consisting of Der p 1, Der f 1, Der p 2 and Der f 2, respectively, in said subsequent batch of said pharmaceutical composition has a batch-to-batch consistency coefficient of variation of less than 25%.

2. A method as defined in claim 1, wherein several of said active ingredient mixtures obtained from step (d) are combined.

3. A method as defined in claim 1, wherein step (f) is performed at least two times, wherein the ratio of active ingredients selected from the group consisting of Der p 1, Der f 1, Der p 2 and Der f 2 in said subsequent batches of said pharmaceutical composition have a batch-to-batch consistency coefficient of variation of less than 25%.

4. A method as defined in claim 1, wherein to obtain at least two active ingredients Der f 1 and Der f 2 step (a) comprises separating from at least one culture of Der f mites, (i) a fraction of Der f mite bodies, comprising greater than 70% v/v Der f mite bodies and (ii) a fraction of Der f faecal particles.

5. A method as defined in claim 1, wherein to obtain at least two active ingredients Der p 1 and Der p 2 step (a) comprises separating from at least one culture of Der p mites, (i) a fraction of Der p mite bodies, comprising greater than 70% v/v Der p mite bodies and (ii) a fraction of Der p faecal particles.

6. A method as defined in claim 1, wherein said multiple batches of pharmaceutical composition comprise the active ingredients Der f 1, Der f 2, Der p 1 and Der p 2, and wherein step (a) comprises
   (A) separating from at least one culture of Der p mites, (i) a fraction of Der p mite bodies, comprising greater than 70% v/v Der p mite bodies and (ii) a fraction of Der p faecal particles, and
   (B) separating from at least one culture of Der f mites, (i) a fraction of Der f mite bodies, comprising greater than 70% v/v Der f mite bodies and (ii) a fraction of Der f faecal particles.

7. A method as defined in claim 1, wherein the fraction of Der f faecal particles comprises greater than 70% v/v Der f mite faecal particles.

8. A method as defined in claim 1, wherein the fraction of Der p faecal particles comprises greater than 70% v/v Der p mite faecal particles.

9. A method as defined in claim 1, wherein fraction (a)1(i) or (a)3(B)(i) comprises greater than 90% v/v Der f mite bodies and fraction (a)1(ii) or (a)3(B)(ii) comprises greater than 90% v/v Der f mite faecal particles.

10. A method as defined in claim 1, wherein fraction (a)1 (i), or (a)3(B)(i) comprises greater than 98% v/v Der f mite bodies and fraction (a)1(ii), or (a)3(B)(ii) comprises greater than 98% v/v Der f faecal particles.

11. A method as defined in claim 1, wherein fraction (a)1(i) or (a)3(B)(i) comprises greater than 95% v/v Der f mite bodies and fraction (a)1(ii) or (a)3(B)(ii) comprises greater than 90% v/v Der f faecal particles.

12. A method as defined in claim 1, wherein fraction (a)2(i) or (a)3(A)(i) comprises greater than 90% v/v Der p mite bodies and fraction (a)2(ii) or (a)3(A)(ii) comprises greater than 90% v/v Der p mite faecal particles.

13. A method as defined in claim 1, wherein fraction (a)2(i) or (a)3(A)(i) comprises greater than 98% v/v Der p mite bodies and fraction (a)2(ii) or (a)3(A)(ii) comprises greater than 98% v/v Der p mite faecal particles.

14. A method as defined in claim 1, wherein fraction (a)2(i) or (a)3(A)(i) comprises greater than 95% v/v Der p mite bodies and fraction (a)2(ii) or (a)3(A)(ii) comprises greater than 90% v/v Der p faecal particles.

15. A method as defined in claim 1, wherein said coefficient of variation is less than 20%.

16. A method as defined in claim 1, wherein said coefficient of variation is less than 15%.

17. A method as defined in claim 1, wherein said coefficient of variation is less than 10%.

18. A method as defined in claim 1, wherein said coefficient of variation is less than 7.5%.

19. A method as defined in claim 1, wherein said pharmaceutical composition has a group 1 to group 2 mite allergen weight ratio ranging from 1:0.6 to 1:1.6.

20. A method as defined in claim 1, wherein said pharmaceutical composition has a group 1 to group 2 mite allergen weight ratio ranging from 1:0.7 to 1:1.5.

21. A method as defined in claim 1, wherein said pharmaceutical composition has a group 1 to group 2 mite allergen weight ratio ranging from 1:0.8 to 1:1.4.

22. A method as defined in claim 1, wherein said pharmaceutical composition has a group 1 to group 2 mite allergen weight ratio ranging from 1:0.9 to 1:1.3.

23. A method as defined in claim 1, wherein said pharmaceutical composition has a group 1 to group 2 mite allergen weight ratio ranging from 1:0.95 to 1:1.2.

24. A method as defined in claim 1, wherein said pharmaceutical composition has a group 1 to group 2 mite allergen weight ratio ranging from 1:0.98 to 1:1.15.

25. A method as defined in claim 1, wherein said pharmaceutical composition contains Der f 1, Der f 2, Der p 1 and Der p 2 in a weight ratio of 1:1:1:1 subject to said coefficient of variation.

26. A method of treating a patient allergic to dust mites with at least one dose of a pharmaceutical composition from a first batch and at least one dose of a pharmaceutical composition from a subsequent batch, wherein each batch of said pharmaceutical composition comprises at least two active ingredients selected from the group consisting of Der p 1, Der f 1, Der p 2 and Der f 2, and wherein the ratio of active ingredients selected from the group consisting of Der p 1, Der f 1, Der p 2 and Der f 2, respectively in said pharmaceutical composition has a batch-to-batch consistency coefficient of variation of less than 25%; said method comprising:
   A) administering to said patient a pharmaceutical composition prepared by a method comprising:
      (a) separating at least two dust mite fractions from a dust mite culture, said separating step comprising:
         1) separating from at least one culture of Der f mites comprising Der f 1 and Der f 2 allergens, (i) a fraction of Der f mite bodies, comprising greater than 70% v/v Der f mite bodies and (ii) a fraction of Der f faecal particles; or
         2) separating from at least one culture of Der p mites comprising Der p 1 and Der p 2 allergens, (i) a fraction of Der p mite bodies, comprising greater than 70% v/v Der p mite bodies and (ii) a fraction of Der p faecal particles; or
         3) (A) separating from at least one culture of Der p mites comprising Der p 1 and Der p 2 allergens, (i) a fraction of Der p mite bodies, comprising greater than 70% v/v Der p mite bodies and (ii) a fraction of Der p faecal particles, and
         (B) separating from at least one culture of Der f mites comprising Der f 1 and Der f 2 allergens, (i) a fraction of Der f mite bodies, comprising greater than 70% v/v Der f mite bodies and (ii) a fraction of Der f faecal particles;
      (b) extracting, from each of said fractions from step (a) group 1, group 2, or groups 1 and 2 mite allergens to obtain mite allergen extracts comprising at least two active ingredients selected from the group consisting of Der f 1, Der f 2, Der p 1, and Der p 2;
      (c) measuring at least the amount of group 1, group 2 or group 1 and group 2 mite allergens in each extract from step (b);
      (d) combining amounts of said extracts from step (b) to yield an active ingredient mixture having a first ratio of active ingredients;
      (e) formulating said active ingredient mixture from step (d) into said first batch of said pharmaceutical composition comprising at least two active ingredients selected from the group consisting of Der p 1, Der f 1, Der p 2 and Der f 2;
   B) subsequently administering to said patient a pharmaceutical composition prepared by a method comprising:

(f) separating at least two dust mite fractions, from at least one of the same or different mite cultures, said separating step comprising:
  1) separating from at least one culture of Der f mites comprising Der f 1 and Der f 2 allergens, (i) a fraction of Der f mite bodies, comprising greater than 70% v/v Der f mite bodies and (ii) a fraction of Der f faecal particles; or
  2) separating from at least one culture of Der p mites comprising Der p 1 and Der p 2 allergens, (i) a fraction of Der p mite bodies, comprising greater than 70% v/v Der p mite bodies and (ii) a fraction of Der p faecal; or
  3) (A) separating from at least one culture of Der p mites comprising Der p 1 and Der p 2 allergens, (i) a fraction of Der p mite bodies, comprising greater than 70% v/v Der p mite bodies and (ii) a fraction of Der p faecal particles, and
    (B) separating from at least one culture of Der f mites comprising Der f 1 and Der f 2 allergens, (i) a fraction of Der f mite bodies, comprising greater than 70% v/v Der f mite bodies and (ii) a fraction of Der f faecal particles;
(g) extracting, from each of said fraction from step (f), group 1, group 2, or groups 1 and 2 mite allergens to obtain a mite allergen extract comprising at least two active ingredients selected from the group consisting of Der f 1, Der f 2, Der p 1, and Der p 2;
(h) measuring at least the amount of group 1, group 2 or group 1 and group 2 mite allergens in each extract from step (g);
(i) combining amounts of said extracts from step (g) to yield an active ingredient mixture having a ratio of active ingredients that has a coefficient of variability of less than 25% in relation to said first ratio of active ingredients; and
(j) formulating said active ingredient mixture from step (i) into a subsequent batch of said pharmaceutical composition wherein the ratio of active ingredients selected from the group consisting of Der p 1, Der f 1, Der p 2 and Der f 2, respectively, in said subsequent batch of said pharmaceutical composition has a batch-to-batch consistency coefficient of variation of less than 25%.

27. A method of treating a patient having allergic rhinitis and/or allergic asthma with at least one dose of a pharmaceutical composition from a first batch and at least one dose of a pharmaceutical composition from a subsequent batch, wherein each batch of said pharmaceutical composition comprises at least two active ingredients selected from the group consisting of Der p 1, Der f 1, Der p 2 and Der f 2, and wherein the ratio of active ingredients selected from the group consisting of Der p 1, Der f 1, Der p 2 and Der f 2, respectively in said pharmaceutical composition has a batch-to batch consistency coefficient of variation of less than 25%; said method comprising:
  A) administering to said patient a pharmaceutical composition prepared by a method comprising:
    (a) separating at least two dust mite fractions from a dust mite culture, said separating step comprising:
      1) separating from at least one culture of Der f mites, comprising Der f 1 and Der f 2 allergens, (i) a fraction of Der f mite bodies, comprising greater than 70% v/v Der f mite bodies and (ii) a fraction of Der f faecal particles; or
      2) separating from at least one culture of Der p mites, comprising Der p 1 and Der p 2 allergens, (i) a fraction of Der p mite bodies, comprising greater than 70% v/v Der p mite bodies and (ii) a fraction of Der p faecal particles; or
      3) (A) separating from at least one culture of Der p mites, comprising Der p 1 and Der p 2 allergens, (i) a fraction of Der p mite bodies, comprising greater than 70% v/v Der p mite bodies and (ii) a fraction of Der p faecal particles, and
        (B) separating from at least one culture of Der f mites, comprising Der f 1 and Der f 2 allergens, (i) a fraction of Der f mite bodies, comprising greater than 70% v/v Der f mite bodies and (ii) a fraction of Der f faecal particles;
    (b) extracting, from each of said fractions from step (a) group 1, group 2, or groups 1 and 2 mite allergens to obtain mite allergen extracts comprising at least two active ingredients selected from the group consisting of Der f 1, Der f 2, Der p 1, and Der p 2;
    (c) measuring at least the amount of group 1, group 2 or group 1 and group 2 mite allergens in each extract from step (b);
    (d) combining amounts of said extracts from step (b) to yield an active ingredient mixture having a first ratio of active ingredients;
    (e) formulating said active ingredient mixture from step (d) into said first batch of pharmaceutical composition comprising at least two active ingredients selected from the group consisting of Der f 1, Der f 2, Der p 1, and Der p 2;
  B) subsequently administering to said patient a pharmaceutical composition prepared by a method comprising:
    (f) separating at least two dust mite fractions, from at least one of the same or different mite cultures
      1) separating from at least one culture of Der f mites comprising Der f 1 and Der f 2 allergens, (i) a fraction of Der f mite bodies, comprising greater than 70% v/v Der f mite bodies and (ii) a fraction of Der f faecal particles;
      2) separating from at least one culture of Der p mites comprising Der p 1 and Der p 2 allergens, (i) a fraction of Der p mite bodies, comprising greater than 70% v/v Der p mite bodies and (ii) a fraction of Der p faecal particles; or
      3) (A) separating from at least one culture of Der p mites comprising Der p 1 and Der p 2 allergens, (i) a fraction of Der p mite bodies, comprising greater than 70% v/v Der p mite bodies and (ii) a fraction of Der p faecal particles, and
        (B) separating from at least one culture of Der f mites comprising Der f 1 and Der f 2 allergens, (i) a fraction of Der f mite bodies, comprising greater than 70% v/v Der f mite bodies and (ii) a fraction of Der f faecal particles;
    (g) extracting, from each of said fraction from step (f), group 1, group 2, or groups 1 and 2 mite allergens to obtain a mite allergen extract comprising at least two active ingredients selected from the group consisting of Der f 1, Der f 2, Der p 1, and Der p 2;
    (h) measuring at least the amount of group 1, group 2 or group 1 and group 2 mite allergens in each extract from step (g);
    (i) combining amounts of said extracts from step (g) to yield an active ingredient mixture having a ratio of active ingredients that has a coefficient of variability of less than 25% in relation to said first ratio of active ingredients; and (j) formulating said active ingredient mixture from step (i) into said subsequent batch of said pharmaceutical composition wherein the ratio of active ingredients selected from the group consisting of Der p 1, Der f 1, Der p 2 and Der f 2, respectively, in said subsequent batch of the pharmaceutical composition has a batch-to-batch consistency coefficient of variation of less than 25%.

28. The method of claim 1 wherein said ratio of active ingredients having a batch-to-batch consistency coefficient of variation of less than 25% is the group 1 to group 2 mite allergen weight ratio.

29. The method of claim 26 wherein said ratio of active ingredients having a batch-to-batch consistency coefficient of variation of less than 25% is the group 1 to group 2 mite allergen weight ratio.

30. The method of claim 27 wherein said ratio of active ingredients having a batch-to-batch consistency coefficient of variation of less than 25% is the group 1 to group 2 mite allergen weight ratio.

31. The method of claim 1 wherein said multiple batches of pharmaceutical composition comprise Der p 1, Der f 1, Der p 2 and Der f 2 as active ingredients.

32. The method of claim 26 wherein said first batch and said subsequent batches of pharmaceutical composition comprise Der p 1, Der f 1, Der p 2 and Der f 2 as active ingredients.

33. The method of claim 27 wherein said first batch and said subsequent batches of pharmaceutical composition comprise Der p 1, Der f 1, Der p 2 and Der f 2 as active ingredients.

34. The method according to claim 1, wherein a fraction of mite bodies and/or wherein a fraction of faecal particles in step a), each comprises below 10% v/v of mite culture medium.

35. The method according to claim 1, wherein the mite body fraction in step a) comprises up to 20% v/v mite parts, faecal particles, and mite medium.

36. The method according claim 1, wherein the mite faecal fraction in step a) comprises up to 20% v/v mite parts, and mite medium.

37. The method according claim 1, wherein the fraction(s) of mite bodies and the fraction(s) of mite faecal particles in step a) is isolated from mite culture(s) by sieving of respectively Der p and/or Der f mite culture(s).

38. The method according to claim 1, wherein said pharmaceutical composition contains from 3 to 8 µg Der p 1, from 3 to 8 µg Der p 2, from 3 to 8 µg Der f 1, and from 3 to 8 µg Der f 2.

39. The method according to claim 1, wherein the pharmaceutical product is a compressed or non-compressed sublingual tablet(s) comprising the extract(s) or allergoids prepared from extract(s), a liquid sublingual product comprising the extract(s) or allergoids prepared from extract(s), or a liquid product for injection comprising the extract(s) or allergoids prepared from extract(s).

40. The method according to claim 1, wherein the pharmaceutical product is a fast dissolving sublingual tablet which comprises an extract.

41. The method according to claim 1, wherein step a) comprises:
  i) subjecting the mite body fraction(s) of claim 1 to density centrifugation in a first liquid medium having a higher density than the mite bodies and a lower density than the culture media particles and wherein group 1 and group 2 allergens are not extracted from the mite bodies; followed by
  ii) collecting mite bodies from the surface of said first liquid medium, and
  iii) repeating step i) and ii) until the desired purity of the mite bodies have been achieved, optionally followed by washing of the mite bodies to remove said first liquid with a second liquid that does not extract group 1 and group 2 allergen from the mite bodies.

42. The method according to claim 41, wherein the first liquid is anhydrous glycerol.

43. The method according to claim 41, wherein the second liquid is anhydrous ethanol.

* * * * *